United States Patent
Ando et al.

(10) Patent No.: US 6,444,849 B1
(45) Date of Patent: Sep. 3, 2002

(54) AMIDE DERIVATIVES

(75) Inventors: Ryoichi Ando, Kanagawa; Makoto Kawamura, Tokyo; Noriko Chiba; Kazutoshi Watanabe, both of Kanagawa, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/469,354

(22) Filed: Dec. 22, 1999

Related U.S. Application Data

(63) Continuation-in-part of application No. 09/103,500, filed on Jun. 24, 1998, now abandoned.

(30) Foreign Application Priority Data

Jun. 25, 1997 (JP) .............................................. 9-168484

(51) Int. Cl.⁷ ..................... C07C 233/05; C07C 233/65; A61K 31/16
(52) U.S. Cl. ....................... 564/155; 564/152; 564/158; 560/29; 514/616; 514/478
(58) Field of Search ................................. 514/478, 616; 560/29; 564/152, 155, 158

(56) References Cited

U.S. PATENT DOCUMENTS

| | | | |
|---|---|---|---|
| 4,666,943 A | 5/1987 | Noguchi et al. | |
| 5,039,805 A | 8/1991 | Alig et al. | |
| 5,280,014 A | * 1/1994 | Jacobson et al. | |
| 5,280,044 A | 1/1994 | Crowley et al. | |

FOREIGN PATENT DOCUMENTS

| EP | 0184822 | * 6/1986 |
|---|---|---|
| JP | 57-7455 | 1/1982 |
| JP | 59116255 | 7/1984 |
| JP | 8-12576 | 1/1996 |
| WO | 94/24151 | 10/1994 |
| WO | 97/04770 | 2/1997 |
| WO | 97/11069 | 3/1997 |
| WO | 97/29079 | 8/1997 |

OTHER PUBLICATIONS

Conn et al, J. Am. Chem. Soc., 115, pp 3548–3557, 1993.*
Ashton et al, J. Med. Chem., vol. 16, No. 5, pp 453–456, 1973.*
Skorcz, J. Med. Chem., vol. 14, No. 8, pp 775–776, 1971.*
Conn et al, J. Am. Chem. Soc., 115, pp 3548–57, 1993.*
Derwent abstract No. 84–203908 of JP 59–116255, published Jul. 5, 1984.
Patent abstract of Japan, vol. 096, No. 005, published May 31, 1996, of JP 8-12576, published Jan. 16, 1996.
CONN et al., "Convergent Functional Groups. 13 High–Affinity Complexation of Adenosine Derivatives within Induced Binding Pockets", *J. Am. Chem. Soc.*, 115, pp. 3548–3557 (1993).
An English Language abstract of JP 57–7455, 1982.
Molecular Medicine, vol. 31, pp. 1304–1374, 1994.

* cited by examiner

Primary Examiner—Shailendra Kumar
(74) Attorney, Agent, or Firm—Greenblum & Bernstein, P.L.C.

(57) ABSTRACT

A compound represented by the following general formula (1);

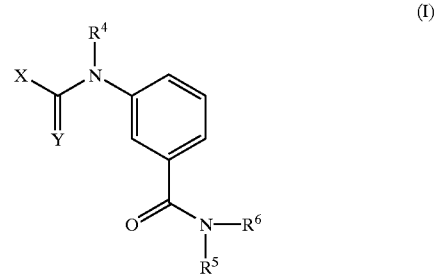

(I)

wherein X represents $R^1(R^2)(R^3)C$— where $R^1$ represents a $C_3$–$C_8$ cycloalkyl group, an optionally substituted $C_6$–$C_{14}$ aryl group, an optionally substituted heterocyclic residue, an optionally substituted $C_6$–$C_{14}$ aryloxy group, or an optionally substituted $C_7$–$C_{15}$ arylmethyl group; $R^2$ and $R^3$ independently represent hydrogen atom or a $C_1$–$C_5$ alkyl group, or $R^2$ and $R^3$ may combine to represent a $C_2$–$C_7$ alkylene group; or X represents $R^7$—A— wherein $R^7$ represents (i) a C1–C10 alkyl group which may optionally be substituted with an optionally substituted C6–C14 aryl group, an optionally substituted fluorenyl group or an optionally substituted heterocyclic group, (ii) an optionally substituted C6–C14 aryl group or (iii) an optionally substituted heterocyclic group, and A represents an oxygen atom or —N—$R^8$ where $R^8$ represents hydrogen atom or a C1–C5 alkyl group, Y represents an oxygen atom or a sulfur atom, $R^4$ and $R^5$ independently represent hydrogen atom or a $C_1$–$C_5$ alkyl group; and $R^6$ represents hydrogen atom, a $C_1$–$C_5$ alkyl group which may optionally be substituted with a hydroxyl group, a hydroxyl group or a $C_1$–$C_5$ alkoxy group, provided that the compounds wherein $R^7$ is a benzyl group, A and Y are an oxygen atom, $R^4$ and $R^5$ are hydrogen atom, and $R^6$ is a propyl group are excluded, or a salt thereof, or a solvate thereof or a hydrate thereof.

29 Claims, No Drawings

AMIDE DERIVATIVES

CROSS-REFERENCE TO RELATED APPLICATIONS

The present application is a continuation-in-part of U.S. application Ser. No. 09/103,500, filed Jun. 24, 1998, now abandoned, and expressly incorporates by reference herein the entire disclosure of U.S. application Ser. No. 09/103,500.

TECHNICAL FIELD

The present invention relates to novel amide derivatives having strong antibacterial activity against Helicobacter pylori.

BACKGROUND ART

Helicobacter pylori is a slightly aerobic gram-negative bacterium which was recently isolated from human gastric mucosa, and various published reports suggest its involvement in inflammation of alimentary tract, formation and recurrence of ulcer, and moreover, gastric cancer (Molecular Medicine, Vol. 31, pp. 1304–1374, 1994).

For the treatment of gastrointestinal ulcers, medicaments such as $H_2$ blockers or proton pump inhibitors have been used so far. Since relation between Helicobacter pylori infection and gastric ulcer has been being clarified as explained above, an antibacterial agent such as amoxicillin has become practically used in combination, particularly from a viewpoint of prevention of recurrence. However, in most cases, ordinarily used antibacterial agents fail to achieve complete elimination of the bacteria. In addition, they may affect on intestinal bacterial flora due to their broad antibacterial spectra, and they often cause adverse effects such as diarrhea. Therefore, it has been desired to develop an antibacterial agent having potent antibacterial activity in alimentary tract that is specific against. Helicobacter pylori.

The compound represented by the general formula (I) defined herein below wherein $R^7$ is a benzyl group, and A and Y are an oxygen atom, and $R^4$ and $R^5$ are a hydrogen atom, and $R^6$ is a propyl group, has been reported as intermediates of receptor models (Journal of American Chemical Society, Vol.115, pp. 3548, 1993). However, it has not been known that this compound has an antibacterial activity against Helicobacter pylori.

DISCLOSURE OF THE INVENTION

The inventors of the present invention conducted researches to provide a novel anti-Helicobacter pylori agent, and as a result, they found that the compounds represented by the following general formula have excellent antibacterial activity against Helicobacter pylori and can exhibit potent antibacterial activity in alimentary tract. The present invention was achieved on the basis of these findings.

The present invention thus provides amide derivatives represented by the following general formula (I) and salts thereof, and solvates thereof and hydrates thereof:

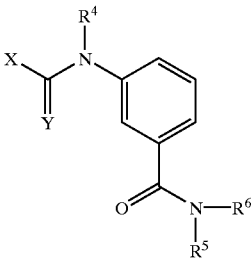

wherein X represents $R^1(R^2)(R^3)C-$ where $R^1$ represents a $C_6$–$C_8$ cycloalkyl group, an optionally substituted $C_6$–$C_{14}$ aryl group, an optionally substituted heterocyclic residue wherein the heterocyclic residue is one of furan ring, dihydrofuran ring, tetrahydrofuran ring, pyran ring, dihydropyran ring, tetrahydropyran ring, benzofuran ring, dihydrobenzofuran ring, isobenzofuran ring, chromene ring, chroman ring, isochroman ring, thiophene ring, benzothiophene ring, pyrrole ring, pyrroline ring, pyrrolidine ring, imidazole ring, imidazoline ring, imidazolidine ring, pyrazole ring, pyrazoline ring, pyrazolidine ring, triazole ring, tetrazole ring, pyridine ring, pyridineoxide ring, piperidine ring, pyrazine ring, piperazine ring, pyrimidine ring, pyridazine ring, indolizine ring, indole ring, indoline ring, isoindole ring, isoindoline ring, indazole ring, benzimidazole ring, purine ring, quixolizine ring, quinoline ring, phthalazine ring, naphthylidine ring, quinoxaline ring, quinazoline ring, cinnoline ring, pteridine ring, oxazole ring, oxazolidine ring, isoxazole ring, isoxazolidine ring, thiazole ring, thiazylidine ring, isothiazole ring, isothiazolidine ring, dioxane ring, dithian ring, morpholine ring, and thiomorpholine ring, an optionally substituted $C_6$–$C_{14}$ aryloxy group, or an optionally substituted $C_7$–$C_{15}$ arylmethyl group; $R^2$ and $R^3$ independently represent hydrogen atom or a $C_1$–$C_5$ alkyl group, or $R^2$ and $R^3$ may combine to represent a $C_2$–$C_7$ aLkylene group; or X represents $R^7-A-$ wherein $R^7$ represents (i) a C1–C10 alkyl group which may optionally be substituted with an optionally substituted C6–C14 aryl group, an optionally substituted fluorenyl group or an optionally substituted heterocyclic group, (ii) an optionally substituted C6–C14 aryl group or (iii) an optionally substituted heterocyclic group, and A represents an oxygen atom or $-N-R^8$ where $R^8$ represents hydrogen atom or a C1–C5 alkyl group, Y represents an oxygen atom or a sulfur atom, $R^4$ and $R^5$ independently represent hydrogen atom or a $C_1$–$C_5$ alkyl group; and $R^6$ represents hydrogen atom, a $C_1$–$C_6$ alkyl group which may optionally be substituted with a hydroxyl group, a hydroxyl group or a $C_1$–$C_6$ alkoxy group, provided that the compounds wherein $R^7$ is a benzyl group, A and Y are an oxygen atom, $R^4$ and $R^5$ are hydrogen atom, and $R^6$ is a propyl group are excluded, or a salt thereof, or a solvate thereof or a hydrate thereof.

According to another aspect of the present invention, the present invention provides medicaments, preferably for the treatment of gastric diseases, e.g., gastritis, gastric ulcer, and gastric cancer, which comprise as an active ingredient a substance selected from the group consisting of the aforementioned amide derivatives and pharmaceutically acceptable salts thereof, and solvates thereof and hydrates thereof. The medicaments are preferably provided as pharmaceutical compositions comprising the aforementioned substance as an active ingredient together with one or more pharmaceutically acceptable additives. These medicaments can be used as anti-Helicobacter pylori agents for therapeutic and/or preventive treatment of digestive diseases related to Helicobacter pylori infections for example, gastritis, gastric ulcer, gastric cancer, stomach malignant lymphoma, MALT lymphoma, duodenal ulcer, duodenal carcinoma and the like.

According to further aspects of the present invention, there are provided a method for treating digestive diseases related to Helicobacter pylori infection which comprises the step of administering to a mammal including a human a therapeutically effective amount of a substance selected from the group consisting of the aforementioned amide derivatives and pharmaceutically acceptable salts thereof, and solvates thereof and hydrates thereof and a s of a substance selected from the group consisting of the aforementioned amide derivatives and pharmaceutically acceptable salts thereof, and solvates thereof and hydrates thereof for the manufacture of the above medicaments.

BEST MODE FOR CARRYING OUT THE INVENTION

In the general formula (I), examples of the $C_6$–$C_8$ cycloalkyl group represented by $R^1$ include, for example, cyclopropyl group, cyclobutyl group, cyclopentyl group, cyclohexyl group, cycloheptyl group, and cyclooctyl group. Examples of the $C_6$–$C_{14}$ aryl group include, for example, aromatic hydrocarbon groups consisting of one ring or two to approximately three condensed aromatic rings such as phenyl group, naphthyl group, and anthryl group.

As the residue of a heterocyclic compound, residues of heterocyclic compounds containing 1 to 4 heteroatoms selected from oxygen atom, sulfur atom, and nitrogen atom, and having 5 to 10 ring-membered atoms in total can be used. More specifically, examples of the residues of heterocyclic compounds include, for example, furan ring, dihydrofuran ring, tetrahydrofuran ring, pyran ring, dihydropyran ring, tetrahydropyran ring, benzofuran ring, dihydrobenzofuran ring, isobenzofuran ring, chromene ring, chroman ring, isochroman ring, thiophene ring, benzothiophene ring, pyrrole ring, pyrroline ring, pyrrolidine ring, imidazole ring, imidazoline ring, imidazohdine ring, pyrazole ring, pyrazoline ring, pyrazolidine ring, triazole ring, tetrazole ring, pyridine ring, pyridineoxide ring, piperidine ring, pyrazine ring, piperazine ring, pyrimidine ring, pyridazine ring, indolizine ring, indole ring, indoline ring, isoindole ring, isoindoline ring, indazole ring, benzimidazole ring, purine ring, quinolie ring, quinoline ring, phthalazine ring, naphthylidine ring, quinoxaline ring, quinazoline ring, cinnoline ring, pteridine ring, oxazole ring, oxazolidine ring, isoxazole ring, isoxazolidine ring, thiazole ring, thiazylidine ring, isothiazole ring, isothiaolidine ring, dioxne ring, dithian ring, morpholine ring, and thiomorpholine ring. Examples of the $C_6$–$C_{14}$ aryloxy group include, for example, phenyloxy group, naphihyloxy group, and anthryloxy group, and examples of the $C_7$–$C_{15}$ arylmethyl group include, for example, benzyl group, naphthylmethyl group, and anthrylmethyl group.

The $C_1$–$C_5$ alkyl group independently represented by $R^2$ and $R^3$ may be either a straight or branched chain alkyl, and examples include, for example, methyl group, ethyl group, propyl group, isopropyl group, butyl group, isobutyl group, pentyl group, and isopentyl group. Examples of the $C_2$–$C_7$ alkylene group represented by $R^2$ combined with $R^3$ include, for example, ethylene group, trimethylene group, tetramethylene group, pentamethylene group, bexamethylene group, and heptamethylene group, and these groups may have one or more branched chains.

As the $C_1$–$C_5$ alkyl group represented by $R^4$ and $R^5$, those explained for $R^2$ and $R^5$ can be independently used. In the present invention, $R^4$ and $R^5$ are preferably hydrogen atom.

As the $C_1$–$C_5$ alkyl group represented by $R^6$, those explained for $R^2$ and $R^3$ can be used, and these alkyl groups may be substituted with at least one, preferably one hydroxy group. The $C_1$–$C_5$ alkoxy group represented by $R^6$ may be a straight or branched chain group, and examples include, for example, methoxy group, ethoxy group, propoxy group, isopropoxy group, butoxy group, isobutoxy group, tertbutoxy group, pentyloxy group, and isopentyloxy group. In the present invention, $R^6$ is preferably an alkyl group, more preferably a methyl group.

As the $C_1$–$C_{10}$ alkyl group represented by $R^7$ in the general formula (I) above, those having a straight or branched chain can be used, and examples include methyl group. ethyl group, propyl group, isopropyl group, butyl group, isobutyl group, pentyl group, isopentyl group, hexyl group, isohexyl group, heptyl group, octyl group, nonyl group, and decyl group. These alkyl groups may optionally be substituted with a $C_6$–$C_{14}$ aryl group, a fluorenyl group or a heterocyclic group. The $C_6$–$C_{14}$ aryl group which can be a substituent on the alkyl group represented by $R^7$ includes, for example, a $C_6$–$C_{14}$ aryl group such as phenyl group, naphtyl group or anthryl group. The heterocyclic group which can be a substituent on the alkyl group represented by $R^7$ includes, for example, those described for $R^1$.

As the $C_6$–$C_{14}$ aryl group and the heterocyclic group represented by $R^7$, those described for the substituent on the $C_1$–$C_{10}$ alkyl group can be used.

$R^7$ is preferably a $C_1$–$C_{10}$ alkyl group which may optionally be substituted with an optionally substituted $C_6$–$C_{14}$ aryl group or an optionally substituted heterocyclic group, more preferably a $C_1$–$C_5$ alkyl group which may optionally be substituted with an optionally substituted $C_6$–$C_{14}$ aryl group or an optionally substituted heterocyclic group, still more preferably a methyl group which may optionally be substituted with an optionally substituted C6–C14 aryl group or an optionally substituted heterocyclic group. In the present invention, $R^7$ is particularly preferably a methyl group which is subsituted with an optionally substituted $C_6$–$C_{14}$ aryl group or a methyl group which is substituted with an optionally substituted heterocyclic group.

A represents an oxygen atom or —N—$R^8$ wherein $R^8$ represents hydrogen atom or a $C_1$–$C_5$ alkyl group. The $C_1$–$C_5$ alkyl group represented by $R^8$ includes methyl group, ethyl group, propyl group, isopropyl group, butyl group, isobutyl group, pentyl group, and isopentyl group. A is preferably an oxygen atom or —N—H.

Y represents an oxygen atom or a sulfur atom. Y is preferably an oxygen atom.

The aforementioned aryl group, residue of a heterocyclic compound, aryloxy group, and arylmethyl group may have one or more subituents at arbitrary positions on their rings Examples of substituents include, for example, a halogen atom such as fluorine atom, chlorine atom, and bromine atom; a $C_1$–$C_5$ alkyl group such as methyl group, ethyl group, propyl group, isopropyl group, butyl group, isobutyl group, sec-butyl group, tertbutyl group, pentyl group, isopentyl group, neopentyl group, and tertentyl group; a $C_7$–$C_{15}$ aralkyl group such as benzyl group, phenylethyl group, and naphtbylmethyl group; trifluoromethyl group; a $C_1$–$C_5$ alkoxy group such as methoxy group, ethoxy group, propoxy group, isopropoxy group, butoxy group, isobutoxy group, tert-butoxy group, pentyloxy group, and isopentyloxy group; a $C_7$–$C_{15}$ aralkyloxy group such as benzyloxy group, phenylethyloxy group, and naphthylmethyloxy group; a $C_1$–$C_5$ alkylenedioxy group such as methylenedioxy group, ethylenedioxy group, and propylenedioxy group; hydroxy group; nitro group; a $C_2$–$C_6$ alkylcarbonyloxy group such as acetoxy group, propionyloxy group, butyryloxy group, and valeryloxy group; carboxyl group; a $C_2$–$C_6$ alkoxycarbonyl group such as methoxycarbonyl group, ethoxycarbonyl group, propoxycarbonyl group, isopropoxycarbonyl group, butoxycarbonyl group, isobutoxycarbonyl group, tert-butoxycarbonyl group, and pentyloxycarbonyl group; a $C_7$–$C_{15}$ aralkyloxycarbonyl group such as benzyloxycarbonyl group, phenylethyloxycarbonyl group, and naphthylmethyloxycarbonyl group; oxo group; a $C_2$–$C_6$ alkylcarbonyt group such as acetyl group, propionyl group, butyryl group, and valeryl group; mino group; a $C_1$–$C_5$ monoalkylamino group such as methylamino group, ethylamino group, propylamino group, isopropylamino group, butylaxnino group, isobutylamino group, tertbutylamino group, pentylamino group, and isopentylamino group; a $C_2$–$C_{10}$ dialkylahino group such as dimethylamino group, etbylmethylamino group, diethylamino group, methylpropylamino group, and disopropylnino group; a $C_2$–$C_6$ alkylcarbonylamino group such as acetylamino group, propionylamino group, isopropionylamino group, butyrylamino group, and valerylamino group; a $C_2$–$C_6$ alkylcarbonylamino group such as methoxycarbonylamino group, ethoxycarbonylamino group, propoxycarbonylamino group, isopropoxycarbonylamino group, butoxycarbonylamino group, isobutoxycarbonylamino group, tert-butoxycarbony no group, and pentyloxycarbonylamino group; a $C_7$–$C_{15}$ aralkyloxycarbonylamino group such as benzyloxycarbonylamino group, phenylethyloxycarbonylamino group, and naphthylmethyloxycarbonylamino group; carbamoyl group; a $C_2$–$C_6$ alkylrarbamoyl group such as methylcarbamoyl group, etbylcarbamoyl group, propylcarbamoyl group, butylcarbamoyl group, tertbutylcarbamoyl group, and pentylcarbamoyl group; a $C_6$–$C_{12}$ aryl group such as phenyl group, and naphthyl group and the like.

Among the compounds of the present invention represented by the above formula (I) wherein X is $R^1(R^2)(R^3)$ C—, preferred compounds include those wherein $R^1$ is a $C_6$–$C_{14}$ aryl group which may optionally be substituted, a residue of a heterocyclic compound which may optionally be substituted, a $C_6$–$C_{14}$ aryloxy group which may optionally be subsituted, or a $C_7$–$C_{15}$ arylmethyl group which may optionally be substituted, $R^2$, $R^3$, $R^4$ and $R^5$ are hydrogen atoms $R^6$ is a $C_1$–$C_5$ alkyl group, and Y is an oxygen atom. More preferred compounds include those wherein $R^1$ is a $C_6$–$C_{14}$ aryl group which may optionally be substituted, a residue of a heterocyclic compound which may optionally be substituted, a $C_6$–$C_{14}$ aryloxy group which may optionally be subsituted, or a $C_7$–$C_{15}$ arylmethyl group which may optionally be substituted, $R^2$, $R^3$, $R^4$ and $R^5$ are hydrogen atoms, $R^6$ is methyl group, and Y is an oxygen atom.

Examples of particularly preferred compounds include:
N-(3-methylcarbamoylphenyl)-3-chlorophenylacetamide;
N-(3-methylcarbamoylphenyl)-4-chlorophenylacetamide;
N-(3-methylcarbamoylphenyl)-3-bromophenylacetamide;
N-(3-methylcarbamoylphenyl)-4-bromophenylacetamide;
N-(3-methylcarbamoylphenyl)-3-methylphenylacetamide;
N-(3-methylcarbamoylphenyl)-4-methylphenylacetamide;
N-(3-methylcarbamoylphenyl)-3-methoxyphenylacetamide;
N-(3-methylcarbamoylphenyl)-4-methoxyphenylacetamide;
N-(3-methylcarbamoylphenyl)-3,4,5-trimethoxyphenylacetamide;
N-(3-methylcarbamoylphenyl)-3-benzyloxyphenylacetamide;
N-(3-methylcarbamoylphenyl)-1-naphthylactamide;
N-(3-methylcarbamoylphenyl)-2-naphthylacetamide;
N-(3-methy)carbamoylphenyl)-3-indolylacetamide;
N-(3-methylcarbamoylphenyl)-3-benzothienylacetamide;
N-(3-methylcarbamoylphenyl)-4-benzothienylacetamide;
N-(3-methylcarbamoylphenyl)-3,4-methylenedioxyphenylacetamide;
N-(3-methylcarbamoylphenyl)-2-chilorophenoxyacetanude;
N-(3-methylcarbamoylphenyl)-2,3-dichlorophenoxyacetamide;
N-(3-mcthylcarbaroylpbenyl)-1-naphthyloxyacetamitde;
N-(3-methylcarbamoy)phenyl)-2-naphthyloxyacetamide; and
N-(3-methylcarbamoylphenyl)-3-(2-methoxyphenyl) propionamide.

Among the compounds of the above formula (I) wherein X is $R^7$—A—, preferred. compounds include those wherein $R^4$ and $R^5$ are hydrogen atom, A is an oxygen atom or —N—H and Y is an oxygen atom, or a pharmaceutically acceptable salt thereof, or a solvate thereof or a hydrate thereof. More preferred compounds include those wherein $R^7$ is a methyl group which is substituted with an optionally substituted $C_6$–$C_{14}$ aryl group or heterocyclic group, $R^4$ and $R^5$ are hydrogen atom, $R^6$ is a methyl group, A is an oxygen atom or —N—H and Y is an oxygen atom, or a pharmaceutically acceptable salt thereof, or a solvate thereof or a hydrate thereof.

Particularly preferred compounds include a compound selected from the group consisting of:
N'-methyl-3-(2-chlorobenzyloxycarbonylamino) benzamide;
N'-methyl-3-(4-chlorobenzyloxycarbonylamino) benzamide;
N'-methyl-3-(2,3-dichlorobenzyloxycarbonylamino) benzamide;
N'-methyl-3-(2,6-dichlorobenzyloxycarbonylamino) benzamide;
N'-methyl-3-(2-bromobenzyloxycarbonylamino) benzamide;
N'-methyl-3-(2-methylbenzyloxycarbonylamino) benzamide;
N'-methyl-3-(3-methylbenzyloxycarbonylamino) benzamide;
N'-methyl-3-(4-methylbenzyloxycarbonylamino) benzamide;
N'-methyl-3-(1-naphthylmethoxycarbonylamino) benzamide; and
N'-methyl-3-(2-naphthylbethoxycarbonylamino) benzamide;

or a pharmaceutically acceptable salt thereof, or a solvate thereof or a hydrate thereof.

The amide derivatives of the present invention represented by the above general formula (I) can form a salt. Where one or more acidic groups exist, examples of salts include, for example, metal salts such as lithium salt, sodium salt, potassium salt, magnesium salt, and calcium salt and ammonium salts such as inorganic ammonium salt, methylammonium salt, dimethylammonium salt, trimethylanmionium salt, and dicyclohexylammxuonium salt. Where one or more basic groups exist, examples of salts include, for example, mineral acid salts such as hydrochloride, hydrobromide, sulfate, nitrate, and phosphate, and organic acid salts such as methanesulfonate, benzenesulfonate, p-toluenesulfonate, acetate, propionate, tartrate, fumarate, maleate, malate, oxalate, succinate, citrate, benzoate, mandelate, cinnamate, and lactate. Pharmaceutically acceptable salts are preferred as the active ingredient of the medicaments of the present invention,. The amide derivatives of the present invention represented by the above general formula (I) and salts thereof may also exist as solvates or hydrates. Any substances in the form of salts, solvates, or hydrates as well as compounds in free forms fall within the scope of the present invention.

As to the stereochemistry of asymmetric carbon atoms present in the amide derivatives of the present invention represented by the general formula (I), the atoms can independently be in (S), (R), or (RS) configuration. Isomers in pure forms based on one or more asymmetric carbon atoms, e.g., enantiomers and diastereoisomers, any mixtures of such isomers, racemates and the like fall within the scope of the present invention.

Examples of specific examples of the amide derivatives of the present invention represented by the above general formula (I) wherein X is $R^1(R^2)(R^3)C-$, and Y is an oxygen atom, include those listed in Table 1.

TABLE 1

| Compd. No. | $R^1$ | $R^2$ | $R^3$ | $R^4$ | $R^5$ | $R^6$ |
|---|---|---|---|---|---|---|
| 1 | cyclopropyl | H | H | H | H | $CH_3$ |
| 2 | cyclobutyl | H | H | H | H | $CH_3$ |
| 3 | cyclopentyl | H | H | H | H | $CH_3$ |
| 4 | cyclohexyl | H | H | H | H | $CH_3$ |
| 5 | cycloheptyl | H | H | H | H | $CH_3$ |
| 6 | cyclooctyl | H | H | H | H | $CH_3$ |
| 7 | phenyl | H | H | H | H | $CH_3$ |
| 8 | phenyl | $CH_3$ | H | H | H | $CH_3$ |
| 9 | phenyl | $CH_3$ | $CH_3$ | H | H | $CH_3$ |

TABLE 1-continued

| Compd. No. | R¹ | R² | R³ | R⁴ | R⁵ | R⁶ |
|---|---|---|---|---|---|---|
| 10 | phenyl | $CH_3$ | $CH_3$ | $CH_3$ | H | $CH_3$ |
| 11 | phenyl | —$(CH_2)_4$— | | H | H | $CH_3$ |
| 12 | phenyl | —$(CH_2)_5$— | | H | H | $CH_3$ |
| 13 | 2-F-phenyl | H | H | H | H | $CH_3$ |
| 14 | 3-F-phenyl | H | H | H | H | $CH_3$ |
| 15 | 4-F-phenyl | H | H | H | H | $CH_3$ |
| 16 | 2-Cl-phenyl | H | H | H | H | $CH_3$ |
| 17 | 3-Cl-phenyl | H | H | H | H | $CH_3$ |
| 18 | 4-Cl-phenyl | H | H | H | H | $CH_3$ |
| 19 | 2-Br-phenyl | H | H | H | H | $CH_3$ |
| 20 | 3-Br-phenyl | H | H | H | H | H |

TABLE 1-continued

| Compd. No. | R¹ | R² | R³ | R⁴ | R⁵ | R⁶ |
|---|---|---|---|---|---|---|
| 21 | 3-bromophenyl | H | H | CH$_3$ | H | CH$_3$ |
| 22 | 3-bromophenyl | H | H | H | H | CH$_3$ |
| 23 | 3-bromophenyl | H | H | H | CH$_3$ | CH$_3$ |
| 24 | 3-bromophenyl | H | H | H | H | CH$_2$CH$_3$ |
| 25 | 3-bromophenyl | H | H | H | H | CH$_2$CH$_2$CH$_3$ |
| 26 | 3-bromophenyl | H | H | H | H | (CH$_2$)$_3$CH$_3$ |
| 27 | 3-bromophenyl | H | H | H | H | (CH$_2$)$_4$CH$_3$ |
| 28 | 3-bromophenyl | H | H | H | H | CH$_2$CH$_2$OH |
| 29 | 3-bromophenyl | H | H | H | H | OH |

TABLE 1-continued

| Compd. No. | R¹ | R² | R³ | R⁴ | R⁵ | R⁶ |
|---|---|---|---|---|---|---|
| 30 | 3-Br-phenyl | H | H | H | H | OCH$_3$ |
| 31 | 3-Br-phenyl | H | H | H | H | OCH$_2$CH$_3$ |
| 32 | 3-Br-phenyl | H | H | H | CH$_2$CH$_3$ | CH$_2$CH$_3$ |
| 33 | 4-Br-phenyl | H | H | H | H | CH$_3$ |
| 34 | 3,4-diCl-phenyl | H | H | H | H | CH$_3$ |
| 35 | 3-Cl-4-Br-phenyl | H | H | H | H | CH$_3$ |
| 36 | 3-Br-4-Cl-phenyl | H | H | H | H | CH$_3$ |
| 37 | 3,4-diBr-phenyl | H | H | H | H | CH$_3$ |
| 38 | 3,4,5-triCl-phenyl | H | H | H | H | CH$_3$ |

TABLE 1-continued
| Compd. No. | R¹ | R² | R³ | R⁴ | R⁵ | R⁶ |
|---|---|---|---|---|---|---|
| 39 | 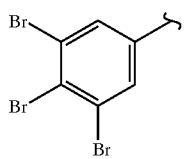 | H | H | H | H | CH₃ |
| 40 | 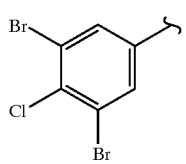 | H | H | H | H | CH₃ |
| 41 | 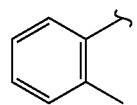 | H | H | H | H | CH₃ |
| 42 | 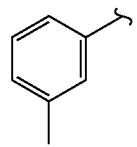 | H | H | H | H | CH₃ |
| 43 | 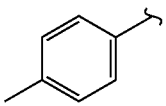 | H | H | H | H | CH₃ |
| 44 | 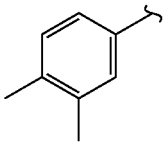 | H | H | H | H | CH₃ |
| 45 | 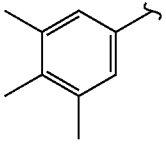 | H | H | H | H | CH₃ |
| 46 | 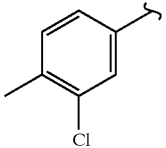 | H | H | H | H | CH₃ |
| 47 | 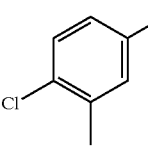 | H | H | H | H | CH₃ |
| 48 | 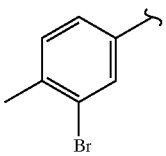 | H | H | H | H | CH₃ |

TABLE 1-continued
| Compd. No. | R¹ | R² | R³ | R⁴ | R⁵ | R⁶ |
|---|---|---|---|---|---|---|
| 49 | 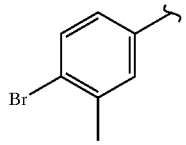 | H | H | H | H | CH₃ |
| 50 | 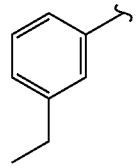 | H | H | H | H | CH₃ |
| 51 | 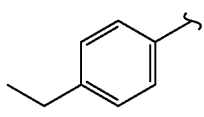 | H | H | H | H | CH₃ |
| 52 | 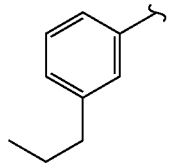 | H | H | H | H | CH₃ |
| 53 | 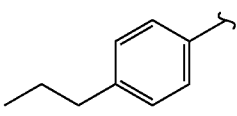 | H | H | H | H | CH₃ |
| 54 | 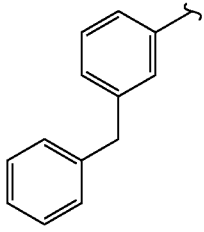 | H | H | H | H | CH₃ |
| 55 | 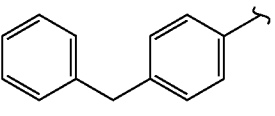 | H | H | H | H | CH₃ |
| 56 | 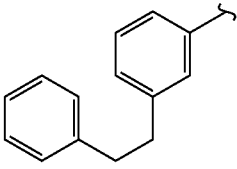 | H | H | H | H | CH₃ |
| 57 | 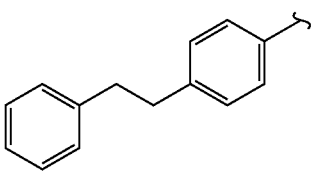 | H | H | H | H | CH₃ |

TABLE 1-continued
| Compd. No. | R¹ | R² | R³ | R⁴ | R⁵ | R⁶ |
|---|---|---|---|---|---|---|
| 58 | 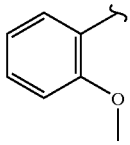 | H | H | H | H | CH₃ |
| 59 | 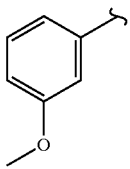 | H | H | H | H | CH₃ |
| 60 | 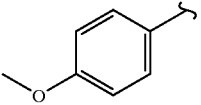 | H | H | H | H | CH₃ |
| 61 | 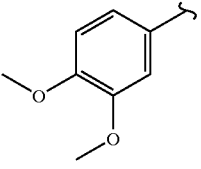 | H | H | H | H | CH₃ |
| 62 | 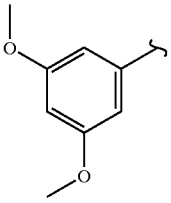 | H | H | H | H | CH₃ |
| 63 | 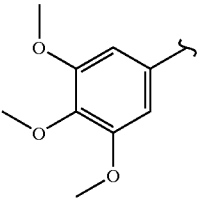 | H | H | H | H | CH₃ |
| 64 | 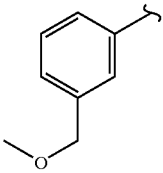 | H | H | H | H | CH₃ |
| 65 | 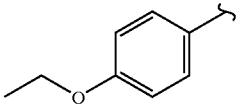 | H | H | H | H | CH₃ |

TABLE 1-continued
| Compd. No. | R¹ | R² | R³ | R⁴ | R⁵ | R⁶ |
|---|---|---|---|---|---|---|
| 66 | 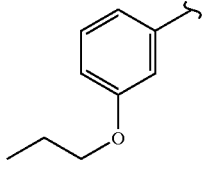 | H | H | H | H | CH₃ |
| 67 | 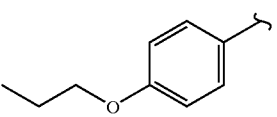 | H | H | H | H | CH₃ |
| 68 | 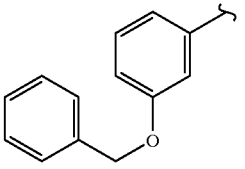 | H | H | H | H | CH₃ |
| 69 | 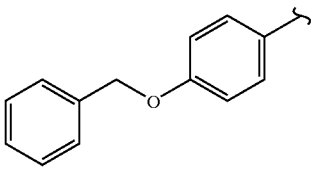 | H | H | H | H | CH₃ |
| 70 | 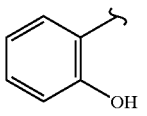 | H | H | H | H | CH₃ |
| 71 | 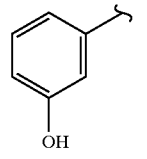 | H | H | H | H | H |
| 72 | 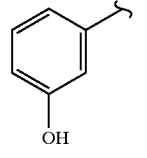 | H | H | H | H | CH₃ |
| 73 | 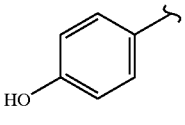 | H | H | H | H | CH₃ |
| 74 | 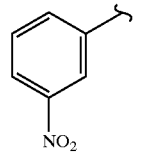 | H | H | H | H | CH₃ |
| 75 | 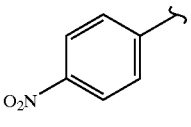 | H | H | H | H | CH₃ |

TABLE 1-continued

| Compd. No. | R¹ | R² | R³ | R⁴ | R⁵ | R⁶ |
|---|---|---|---|---|---|---|
| 76 | 2-aminophenyl | H | H | H | H | CH₃ |
| 77 | 3-aminophenyl | H | H | H | H | CH₃ |
| 78 | 4-acetamidophenyl | H | H | H | H | CH₃ |
| 79 | 2-(methylamino)phenyl | H | H | H | H | CH₃ |
| 80 | 3-(methylamino)phenyl | H | H | H | H | CH₃ |
| 81 | 4-(methylamino)phenyl | H | H | H | H | CH₃ |
| 82 | 2-(dimethylamino)phenyl | H | H | H | H | CH₃ |
| 83 | 3-(dimethylamino)phenyl | H | H | H | H | CH₃ |
| 84 | 4-(dimethylamino)phenyl | H | H | H | H | CH₃ |
| 85 | 2-acetamidophenyl | H | H | H | H | CH₃ |

TABLE 1-continued

| Compd. No. | R¹ | R² | R³ | R⁴ | R⁵ | R⁶ |
|---|---|---|---|---|---|---|
| 86 | 3-(acetylamino)phenyl | H | H | H | H | CH₃ |
| 87 | 4-(acetylamino)phenyl | H | H | H | H | CH₃ |
| 88 | 2-(methoxycarbonylamino)phenyl | H | H | H | H | CH₃ |
| 89 | 3-(methoxycarbonylamino)phenyl | H | H | H | H | CH₃ |
| 90 | 4-(methoxycarbonylamino)phenyl | H | H | H | H | CH₃ |
| 91 | 3-(tert-butoxycarbonylamino)phenyl | H | H | H | H | CH₃ |
| 92 | 4-(tert-butoxycarbonylamino)phenyl | H | H | H | H | CH₃ |
| 93 | 3-(benzyloxycarbonylamino)phenyl | H | H | H | H | CH₃ |

TABLE 1-continued

| Compd. No. | R¹ | R² | R³ | R⁴ | R⁵ | R⁶ |
|---|---|---|---|---|---|---|
| 94 | 4-(benzyloxycarbonylamino)phenyl | H | H | H | H | CH₃ |
| 95 | 2-(methylthio)phenyl | H | H | H | H | CH₃ |
| 96 | 3-(methylthio)phenyl | H | H | H | H | CH₃ |
| 97 | 3-(methylthiomethyl)phenyl | H | H | H | H | CH₃ |
| 98 | 3-(benzylthio)phenyl | H | H | H | H | CH₃ |
| 99 | 4-(benzylthio)phenyl | H | H | H | H | CH₃ |
| 100 | 2-carboxyphenyl | H | H | H | H | CH₃ |
| 101 | 3-carboxyphenyl | H | H | H | H | CH₃ |
| 102 | 4-carboxyphenyl | H | H | H | H | CH₃ |

TABLE 1-continued
| Compd. No. | R¹ | R² | R³ | R⁴ | R⁵ | R⁶ |
|---|---|---|---|---|---|---|
| 103 | 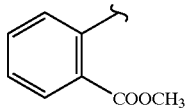 | H | H | H | H | CH₃ |
| 104 |  | H | H | H | H | CH₃ |
| 105 | 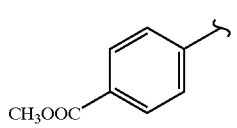 | H | H | H | H | CH₃ |
| 106 | 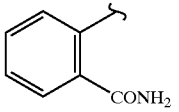 | H | H | H | H | CH₃ |
| 107 |  | H | H | H | H | CH₃ |
| 108 | 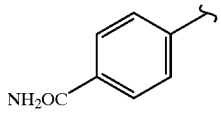 | H | H | H | H | CH₃ |
| 109 |  | H | H | H | H | CH₃ |
| 110 | 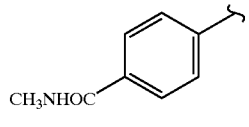 | H | H | H | H | CH₃ |
| 111 | 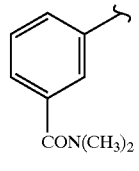 | H | H | H | H | CH₃ |
| 112 | 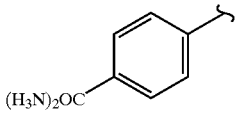 | H | H | H | H | CH₃ |

TABLE 1-continued

| Compd. No. | R¹ | R² | R³ | R⁴ | R⁵ | R⁶ |
|---|---|---|---|---|---|---|
| 113 | 1-naphthyl | H | H | H | H | CH₃ |
| 114 | 2-naphthyl | H | H | H | H | CH₃ |
| 115 | 3-furyl | H | H | H | H | CH₃ |
| 116 | 2-furyl | H | H | H | H | CH₃ |
| 117 | 3-pyrrolyl | H | H | H | H | CH₃ |
| 118 | 2-pyrrolyl | H | H | H | H | CH₃ |
| 119 | 3-thienyl | H | H | H | H | CH₃ |
| 120 | 2-thienyl | H | H | H | H | CH₃ |
| 121 | 2-pyridyl | H | H | H | H | CH₃ |
| 122 | 3-pyridyl | H | H | H | H | CH₃ |
| 123 | 4-pyridyl | H | H | H | H | CH₃ |
| 124 | 2-pyridyl N-oxide | H | H | H | H | CH₃ |

TABLE 1-continued
| Compd. No. | R¹ | R² | R³ | R⁴ | R⁵ | R⁶ |
|---|---|---|---|---|---|---|
| 125 | 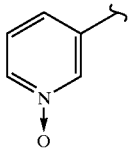 | H | H | H | H | CH₃ |
| 126 | 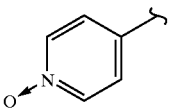 | H | H | H | H | CH₃ |
| 127 | 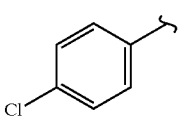 | H | H | H | H | CH₃ |
| 128 | 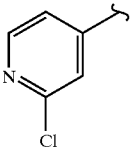 | H | H | H | H | CH₃ |
| 129 | 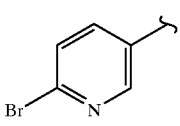 | H | H | H | H | CH₃ |
| 130 | 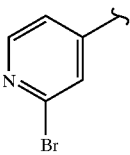 | H | H | H | H | CH₃ |
| 131 | 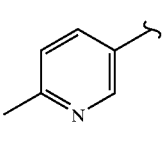 | H | H | H | H | CH₃ |
| 132 | 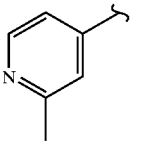 | H | H | H | H | CH₃ |
| 133 | 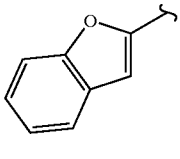 | H | H | H | H | CH₃ |
| 134 | 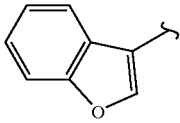 | H | H | H | H | CH₃ |

TABLE 1-continued
| Compd. No. | R¹ | R² | R³ | R⁴ | R⁵ | R⁶ |
|---|---|---|---|---|---|---|
| 135 | 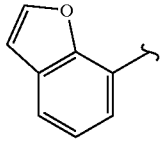 | H | H | H | H | CH$_3$ |
| 136 | 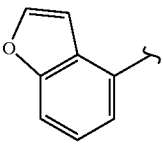 | H | H | H | H | CH$_3$ |
| 137 | 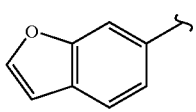 | H | H | H | H | CH$_3$ |
| 138 | 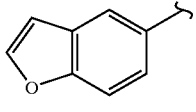 | H | H | H | H | CH$_3$ |
| 139 | 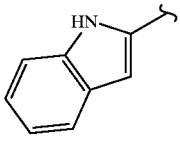 | H | H | H | H | CH$_3$ |
| 140 | 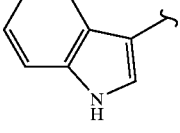 | H | H | H | H | CH$_3$ |
| 141 | 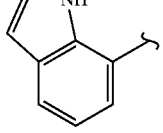 | H | H | H | H | CH$_3$ |
| 142 | 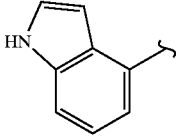 | H | H | H | H | CH$_3$ |
| 143 | 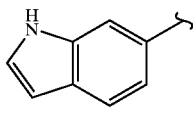 | H | H | H | H | CH$_3$ |
| 144 | 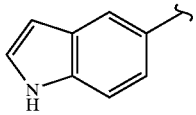 | H | H | H | H | CH$_3$ |

TABLE 1-continued
| Compd. No. | R¹ | R² | R³ | R⁴ | R⁵ | R⁶ |
|---|---|---|---|---|---|---|
| 145 | 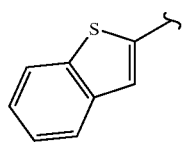 | H | H | H | H | CH₃ |
| 146 | 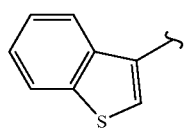 | H | H | H | H | CH₃ |
| 147 | 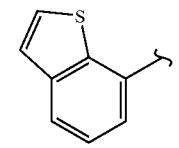 | H | H | H | H | CH₃ |
| 148 | 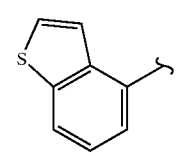 | H | H | H | H | CH₃ |
| 149 | 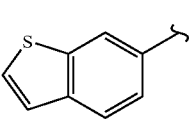 | H | H | H | H | CH₃ |
| 150 | 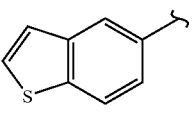 | H | H | H | H | CH₃ |
| 151 | 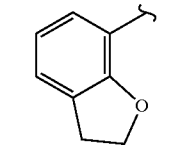 | H | H | H | H | CH₃ |
| 152 | 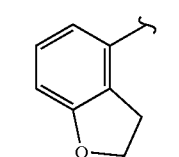 | H | H | H | H | CH₃ |
| 153 | 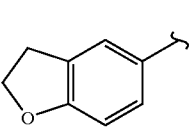 | H | H | H | H | CH₃ |
| 154 | 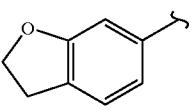 | H | H | H | H | CH₃ |
| 155 | 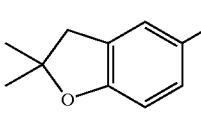 | H | H | H | H | CH₃ |

TABLE 1-continued

| Compd. No. | R¹ | R² | R³ | R⁴ | R⁵ | R⁶ |
|---|---|---|---|---|---|---|
| 156 | 2,2-dimethyl-2,3-dihydrobenzofuran-5-yl | CH₃ | H | H | H | CH₃ |
| 157 | 2,2-dimethyl-2,3-dihydrobenzofuran-5-yl | CH₃ | CH₃ | H | H | CH₃ |
| 158 | benzo[1,3]dioxol-4-yl | H | H | H | H | CH₃ |
| 159 | benzo[1,3]dioxol-5-yl | H | H | H | H | CH₃ |
| 160 | 2,3-dihydrobenzo[1,4]dioxin-5-yl | H | H | H | H | CH₃ |
| 161 | 2,3-dihydrobenzo[1,4]dioxin-6-yl | H | H | H | H | CH₃ |
| 162 | quinolin-8-yl | H | H | H | H | CH₃ |
| 163 | isoquinolin-8-yl | H | H | H | H | CH₃ |
| 164 | isoquinolin-5-yl | H | H | H | H | CH₃ |
| 165 | quinolin-5-yl | H | H | H | H | CH₃ |

TABLE 1-continued

| Compd. No. | R¹ | R² | R³ | R⁴ | R⁵ | R⁶ |
|---|---|---|---|---|---|---|
| 166 | isoquinolin-4-yl | H | H | H | H | CH₃ |
| 167 | isoquinolin-4-yl | H | H | H | H | CH₃ |
| 168 | isoquinolin-1-yl | H | H | H | H | CH₃ |
| 169 | quinolin-2-yl | H | H | H | H | CH₃ |
| 170 | isoquinolin-3-yl | H | H | H | H | CH₃ |
| 171 | quinolin-3-yl | H | H | H | H | CH₃ |
| 172 | quinolin-6-yl | H | H | H | H | CH₃ |
| 173 | isoquinolin-6-yl | H | H | H | H | CH₃ |
| 174 | isoquinolin-7-yl | H | H | H | H | CH₃ |
| 175 | quinolin-7-yl | H | H | H | H | CH₃ |
| 176 | phenoxy | H | H | H | H | CH₃ |

TABLE 1-continued
| Compd. No. | R¹ | R² | R³ | R⁴ | R⁵ | R⁶ |
|---|---|---|---|---|---|---|
| 177 | 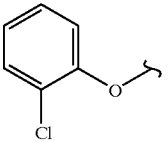 | H | H | H | H | CH₃ |
| 178 | 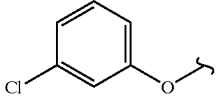 | H | H | H | H | CH₃ |
| 179 | 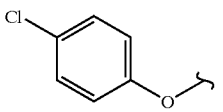 | H | H | H | H | CH₃ |
| 180 | 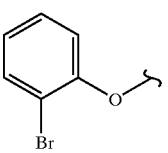 | H | H | H | H | CH₃ |
| 181 | 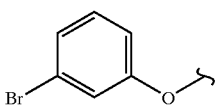 | H | H | H | H | CH₃ |
| 182 | 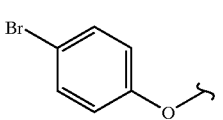 | H | H | H | H | CH₃ |
| 183 | 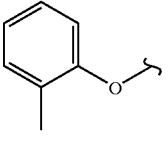 | H | H | H | H | CH₃ |
| 184 | 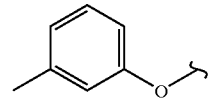 | H | H | H | H | CH₃ |
| 185 | 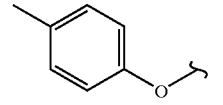 | H | H | H | H | CH₃ |
| 186 | 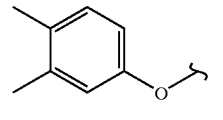 | H | H | H | H | CH₃ |
| 187 | 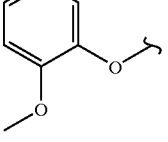 | H | H | H | H | CH₃ |

TABLE 1-continued
| Compd. No. | R¹ | R² | R³ | R⁴ | R⁵ | R⁶ |
|---|---|---|---|---|---|---|
| 188 | 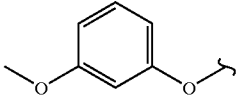 | H | H | H | H | CH₃ |
| 189 | 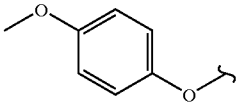 | H | H | H | H | CH₃ |
| 190 | 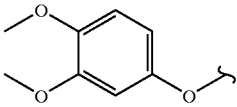 | H | H | H | H | CH₃ |
| 191 | 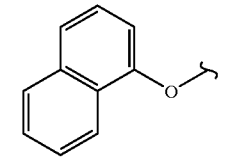 | H | H | H | H | CH₃ |
| 192 | 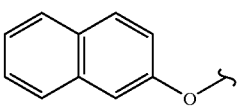 | H | H | H | H | CH₃ |
| 193 | 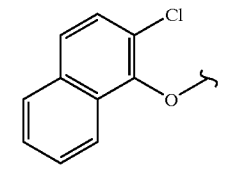 | H | H | H | H | CH₃ |
| 194 | 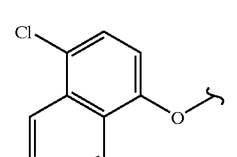 | H | H | H | H | CH₃ |
| 195 | 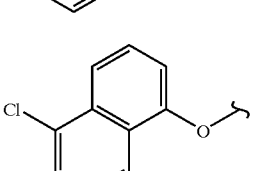 | H | H | H | H | CH₃ |
| 196 | 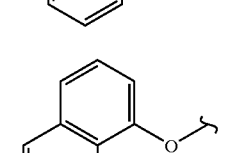 | H | H | H | H | CH₃ |
| 197 | 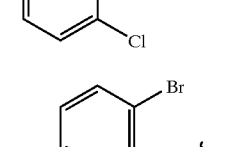 | H | H | H | H | CH₃ |

TABLE 1-continued

| Compd. No. | R¹ | R² | R³ | R⁴ | R⁵ | R⁶ |
|---|---|---|---|---|---|---|
| 198 | 3-chloro-naphthalen-2-yloxy | H | H | H | H | CH₃ |
| 199 | 1-chloro-naphthalen-2-yloxy | H | H | H | H | CH₃ |
| 200 | 6-chloro-naphthalen-2-yloxy | H | H | H | H | CH₃ |
| 201 | 3-methyl-naphthalen-2-yloxy | H | H | H | H | CH₃ |
| 202 | 1-methyl-naphthalen-2-yloxy | H | H | H | H | CH₃ |
| 203 | 2,6-dichloro-phenoxy | H | H | H | H | CH₃ |
| 204 | 2,3-dichloro-phenoxy | H | H | H | H | CH₃ |
| 205 | 2,5-dichloro-phenoxy | H | H | H | H | CH₃ |
| 206 | 2,4-dichloro-phenoxy | H | H | H | H | CH₃ |
| 207 | 2,4,6-trichloro-phenoxy | H | H | H | H | CH₃ |

TABLE 1-continued
| Compd. No. | R¹ | R² | R³ | R⁴ | R⁵ | R⁶ |
|---|---|---|---|---|---|---|
| 208 | 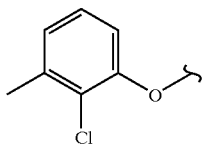 | H | H | H | H | CH₃ |
| 209 | 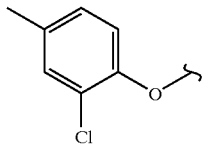 | H | H | H | H | CH₃ |
| 210 | 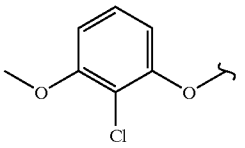 | H | H | H | H | CH₃ |
| 211 | 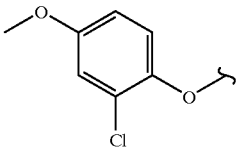 | H | H | H | H | CH₃ |
| 212 | 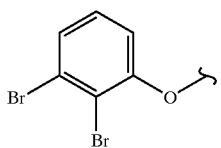 | H | H | H | H | CH₃ |
| 213 | 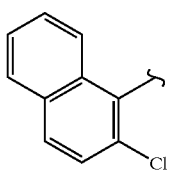 | H | H | H | H | CH₃ |
| 214 | 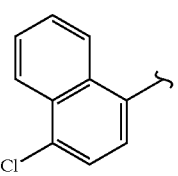 | H | H | H | H | CH₃ |
| 215 | 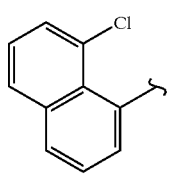 | H | H | H | H | CH₃ |
| 216 | 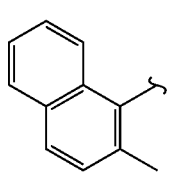 | H | H | H | H | CH₃ |

TABLE 1-continued
| Compd. No. | R¹ | R² | R³ | R⁴ | R⁵ | R⁶ |
|---|---|---|---|---|---|---|
| 217 | 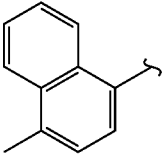 | H | H | H | H | CH₃ |
| 218 | 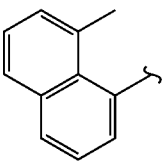 | H | H | H | H | CH₃ |
| 219 | 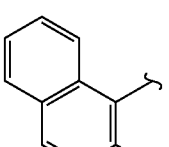 | H | H | H | H | CH₃ |
| 220 | 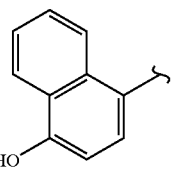 | H | H | H | H | CH₃ |
| 221 | 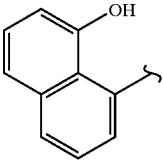 | H | H | H | H | CH₃ |
| 222 | 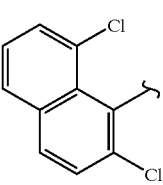 | H | H | H | H | CH₃ |
| 223 | 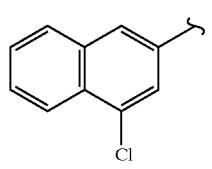 | H | H | H | H | CH₃ |
| 224 | 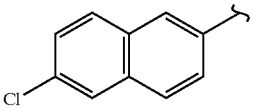 | H | H | H | H | CH₃ |
| 225 | 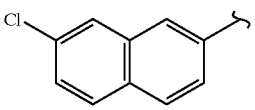 | H | H | H | H | CH₃ |

TABLE 1-continued

| Compd. No. | R¹ | R² | R³ | R⁴ | R⁵ | R⁶ |
|---|---|---|---|---|---|---|
| 226 | 4-methyl-2-naphthyl | H | H | H | H | CH₃ |
| 227 | 6-methyl-2-naphthyl | H | H | H | H | CH₃ |
| 228 | 7-methyl-2-naphthyl | H | H | H | H | CH₃ |
| 229 | 4-methoxy-2-naphthyl | H | H | H | H | CH₃ |
| 230 | 6-methoxy-2-naphthyl | H | H | H | H | CH₃ |
| 231 | 7-methoxy-2-naphthyl | H | H | H | H | CH₃ |
| 232 | 4,5-dichloro-2-naphthyl | H | H | H | H | CH₃ |
| 233 | benzyl | H | H | H | H | CH₃ |
| 234 | 2-chlorobenzyl | H | H | H | H | CH₃ |
| 235 | 3-chlorobenzyl | H | H | H | H | CH₃ |
| 236 | 4-chlorobenzyl | H | H | H | H | CH₃ |

TABLE 1-continued
| Compd. No. | R¹ | R² | R³ | R⁴ | R⁵ | R⁶ |
|---|---|---|---|---|---|---|
| 237 | 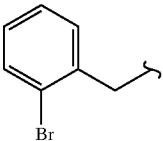 | H | H | H | H | CH₃ |
| 238 | 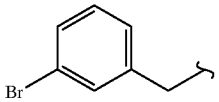 | H | H | H | H | CH₃ |
| 239 | 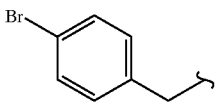 | H | H | H | H | CH₃ |
| 240 | 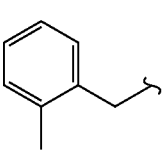 | H | H | H | H | CH₃ |
| 241 | 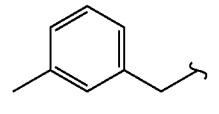 | H | H | H | H | CH₃ |
| 242 | 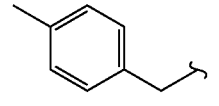 | H | H | H | H | CH₃ |
| 243 | 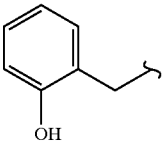 | H | H | H | H | CH₃ |
| 244 | 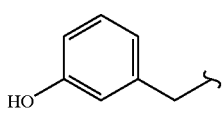 | H | H | H | H | CH₃ |
| 245 | 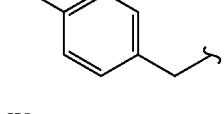 | H | H | H | H | CH₃ |
| 246 | 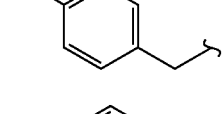 | H | H | H | H | CH₃ |
| 247 | 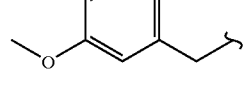 | H | H | H | H | CH₃ |
| 248 | 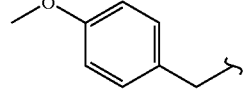 | H | H | H | H | CH₃ |

TABLE 1-continued

| Compd. No. | R¹ | R² | R³ | R⁴ | R⁵ | R⁶ |
|---|---|---|---|---|---|---|
| 249 | 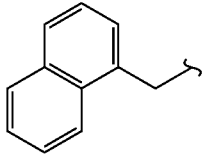 | H | H | H | H | CH₃ |
| 250 | 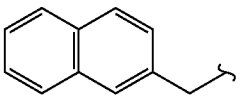 | H | H | H | H | CH₃ |
| 251 | 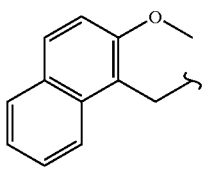 | H | H | H | H | CH₃ |
| 252 | 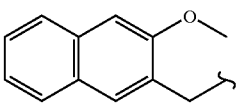 | H | H | H | H | CH₃ |

Examples of specific examples of the amide derivatives of the present invention represented by the above general formula (I) wherein X is $R^7$—A—, include those listed in Table 2.

TABLE 2

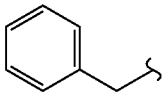

| Compd. No. | R⁷ | A | Y | R⁴ | R⁵ | R⁶ |
|---|---|---|---|---|---|---|
| 1 | CH₃ | O | O | H | H | CH₃ |
| 2 | | NH | O | | | |
| 3 | | O | O | H | H | CH₃ |
| 4 | | O | S | | | |
| 5 | | NH | O | | | |
| 6 | | NH | S | | | |
| 7 | | O | O | H | H | H |
| 8 | | NH | O | | | |
| 9 | | O | O | H | CH₃ | CH₃ |
| 10 | | NH | O | | | |
| 11 | | O | O | H | H | CH₂CH₃ |
| 12 | | NH | O | | | |
| 13 | | O | O | H | H | CH₂CH₂CH₃ |
| 14 | | NH | O | | | |
| 15 | | O | O | CH₃ | H | CH₃ |
| 16 | | NH | O | | | |

TABLE 2-continued

| Compd. No. | R⁷ | A | Y | R⁴ | R⁵ | R⁶ |
|---|---|---|---|---|---|---|
| 17 | 2-F-benzyl | O | O | H | H | CH₃ |
| 18 | 2-F-benzyl | NH | O | | | |
| 19 | 3-F-benzyl | O | O | H | H | CH₃ |
| 20 | 3-F-benzyl | NH | O | | | |
| 21 | 4-F-benzyl | O | O | H | H | CH₃ |
| 22 | 4-F-benzyl | NH | O | | | |
| 23 | 2-Cl-benzyl | O | O | H | H | CH₃ |
| 24 | 2-Cl-benzyl | NH | O | | | |
| 25 | 3-Cl-benzyl | O | O | H | H | CH₃ |
| 26 | 3-Cl-benzyl | NH | O | | | |
| 27 | 4-Cl-benzyl | O | O | H | H | CH₃ |
| 28 | 4-Cl-benzyl | NH | O | | | |
| 29 | 2,3-diCl-benzyl | O | O | H | H | CH₃ |
| 30 | 2,3-diCl-benzyl | NH | O | | | |
| 31 | 2,4-diCl-benzyl | O | O | H | H | CH₃ |
| 32 | 2,4-diCl-benzyl | NH | O | | | |
| 33 | 2,5-diCl-benzyl | O | O | H | H | CH₃ |
| 34 | 2,5-diCl-benzyl | NH | O | | | |
| 35 | 2,6-diCl-benzyl | O | O | H | H | CH₃ |
| 36 | 2,6-diCl-benzyl | NH | O | | | |

TABLE 2-continued

| Compd. No. | R⁷ | A | Y | R⁴ | R⁵ | R⁶ |
|---|---|---|---|---|---|---|
| 37 | 3,5-dichlorobenzyl | O | O | H | H | CH₃ |
| 38 | | NH | O | | | |
| 39 | 3,4-dichlorobenzyl | O | O | H | H | CH₃ |
| 40 | | NH | O | | | |
| 41 | 2-bromobenzyl | O | O | H | H | CH₃ |
| 42 | | NH | O | | | |
| 43 | 3-bromobenzyl | O | O | H | H | CH₃ |
| 44 | | NH | O | | | |
| 45 | 4-bromobenzyl | O | O | H | H | CH₃ |
| 46 | | NH | O | | | |
| 47 | 2-methylbenzyl | O | O | H | H | CH₃ |
| 48 | | NH | O | | | |
| 49 | 3-methylbenzyl | O | O | H | H | CH₃ |
| 50 | | NH | O | | | |
| 51 | 4-methylbenzyl | O | O | H | H | CH₃ |
| 52 | | NH | O | | | |
| 53 | 4-ethylbenzyl | O | O | H | H | CH₃ |
| 54 | | NH | O | | | |
| 55 | 4-propylbenzyl | O | O | H | H | CH₃ |
| 56 | | NH | O | | | |
| 57 | 4-isopropylbenzyl | O | O | H | H | CH₃ |
| 58 | | NH | O | | | |

TABLE 2-continued

| Compd. No. | R⁷ | A | Y | R⁴ | R⁵ | R⁶ |
|---|---|---|---|---|---|---|
| 59 | 4-tert-butylbenzyl | O | O | H | H | CH₃ |
| 60 | 4-tert-butylbenzyl | NH | O | | | |
| 61 | 2-methoxybenzyl | O | O | H | H | CH₃ |
| 62 | 2-methoxybenzyl | NH | O | | | |
| 63 | 3-methoxybenzyl | O | O | H | H | CH₃ |
| 64 | 3-methoxybenzyl | NH | O | | | |
| 65 | 4-methoxybenzyl | O | O | H | H | CH₃ |
| 66 | 4-methoxybenzyl | NH | O | | | |
| 67 | 4-ethoxybenzyl | O | O | H | H | CH₃ |
| 68 | 4-ethoxybenzyl | NH | O | | | |
| 69 | 4-isopropoxybenzyl | O | O | H | H | CH₃ |
| 70 | 4-isopropoxybenzyl | NH | O | | | |
| 71 | 2-nitrobenzyl | O | O | H | H | CH₃ |
| 72 | 2-nitrobenzyl | NH | O | | | |
| 73 | 3-nitrobenzyl | O | O | H | H | CH₃ |
| 74 | 3-nitrobenzyl | NH | O | | | |
| 75 | 4-nitrobenzyl | O | O | H | H | CH₃ |
| 76 | 4-nitrobenzyl | NH | O | | | |
| 77 | 4-chloro-2-nitrobenzyl | O | O | H | H | CH₃ |
| 78 | 4-chloro-2-nitrobenzyl | NH | O | | | |
| 79 | 2-chloro-4-nitrobenzyl | O | O | H | H | CH₃ |
| 80 | 2-chloro-4-nitrobenzyl | NH | O | | | |

TABLE 2-continued
| Compd. No. | R⁷ | A | Y | R⁴ | R⁵ | R⁶ |
|---|---|---|---|---|---|---|
| 81 | 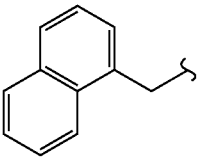 | O | O | H | H | CH₃ |
| 82 | | NH | O | | | |
| 83 | 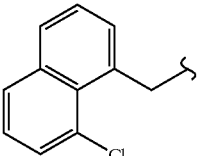 | O | O | H | H | CH₃ |
| 84 | | NH | O | | | |
| 85 | 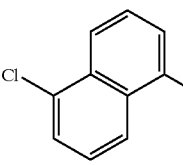 | O | O | H | H | CH₃ |
| 86 | | NH | O | | | |
| 87 | 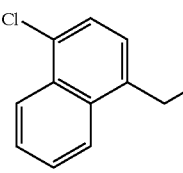 | O | O | H | H | CH₃ |
| 88 | | NH | O | | | |
| 89 | 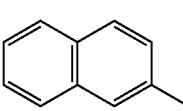 | O | O | H | H | CH₃ |
| 90 | | NH | O | | | |
| 91 | 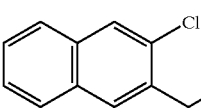 | O | O | H | H | CH₃ |
| 92 | | NH | O | | | |
| 93 | 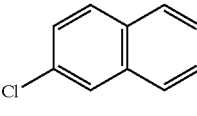 | O | O | H | H | CH₃ |
| 94 | | NH | O | | | |
| 95 | 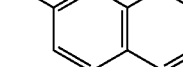 | O | O | H | H | CH₃ |
| 96 | | NH | O | | | |
| 97 | 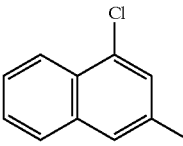 | O | O | H | H | CH₃ |
| 98 | | NH | O | | | |

TABLE 2-continued

| Compd. No. | R⁷ | A | Y | R⁴ | R⁵ | R⁶ |
|---|---|---|---|---|---|---|
| 99 | fluoren-9-ylmethyl | O | O | H | H | CH₃ |
| 100 | | NH | O | | | |
| 101 | pyridin-2-ylmethyl | O | O | H | H | CH₃ |
| 102 | | NH | O | | | |
| 103 | pyridin-3-ylmethyl | O | O | H | H | CH₃ |
| 104 | | NH | O | | | |
| 105 | pyridin-4-ylmethyl | O | O | H | H | CH₃ |
| 106 | | NH | O | | | |
| 107 | pyrimidin-2-ylmethyl | O | O | H | H | CH₃ |
| 108 | | NH | O | | | |
| 109 | pyrimidin-4-ylmethyl | O | O | H | H | CH₃ |
| 110 | | NH | O | | | |
| 111 | 1,3,5-triazin-2-ylmethyl | O | O | H | H | CH₃ |
| 112 | | NH | O | | | |
| 113 | furan-2-ylmethyl | O | O | H | H | CH₃ |
| 114 | | NH | O | | | |
| 115 | furan-3-ylmethyl | O | O | H | H | CH₃ |
| 116 | | NH | O | | | |
| 117 | thiophen-2-ylmethyl | O | O | H | H | CH₃ |
| 118 | | NH | O | | | |
| 119 | thiophen-3-ylmethyl | O | O | H | H | CH₃ |
| 120 | | NH | O | | | |
| 121 | pyrrol-2-ylmethyl | O | O | H | H | CH₃ |
| 122 | | NH | O | | | |

TABLE 2-continued

| Compd. No. | R⁷ | A | Y | R⁴ | R⁵ | R⁶ |
|---|---|---|---|---|---|---|
| 123 | (1H-pyrrol-3-yl)methyl | O | O | H | H | CH₃ |
| 124 | | NH | O | | | |
| 125 | (1-methyl-1H-pyrrol-2-yl)methyl | O | O | H | H | CH₃ |
| 126 | | NH | O | | | |
| 127 | (1-methyl-1H-pyrrol-3-yl)methyl | O | O | H | H | CH₃ |
| 128 | | NH | O | | | |
| 129 | oxazol-2-ylmethyl | O | O | H | H | CH₃ |
| 130 | | NH | O | | | |
| 131 | thiazol-2-ylmethyl | O | O | H | H | CH₃ |
| 132 | | NH | O | | | |
| 133 | benzofuran-2-ylmethyl | O | O | H | H | CH₃ |
| 134 | | NH | O | | | |
| 135 | benzofuran-3-ylmethyl | O | O | H | H | CH₃ |
| 136 | | NH | O | | | |
| 137 | benzo[b]thiophen-2-ylmethyl | O | O | H | H | CH₃ |
| 138 | | NH | O | | | |
| 139 | benzo[b]thiophen-3-ylmethyl | O | O | H | H | CH₃ |
| 140 | | NH | O | | | |
| 141 | CH₃CH₂ | O | O | H | H | CH₃ |
| 142 | | NH | O | | | |
| 143 | 2-phenylethyl | O | O | H | H | CH₃ |
| 144 | | NH | O | | | |
| 145 | 2-(2-chlorophenyl)ethyl | O | O | H | H | CH₃ |
| 146 | | NH | O | | | |

TABLE 2-continued
| Compd. No. | R⁷ | A | Y | R⁴ | R⁵ | R⁶ |
|---|---|---|---|---|---|---|
| 147 | 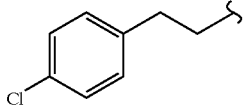 | O | O | H | H | CH₃ |
| 148 | | NH | O | | | |
| 149 | 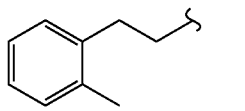 | O | O | H | H | CH₃ |
| 150 | | NH | O | | | |
| 151 | 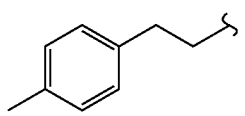 | O | O | H | H | CH₃ |
| 152 | | NH | O | | | |
| 153 | 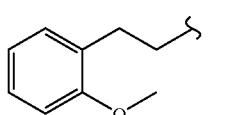 | O | O | H | H | CH₃ |
| 154 | | NH | O | | | |
| 155 | 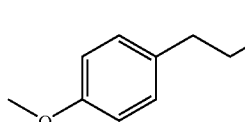 | O | O | H | H | CH₃ |
| 156 | | NH | O | | | |
| 157 | 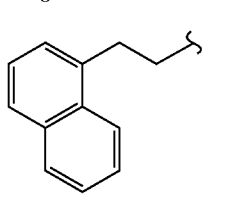 | O | O | H | H | CH₃ |
| 158 | | NH | O | | | |
| 159 | 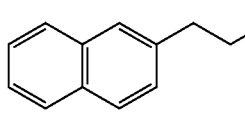 | O | O | H | H | CH₃ |
| 160 | | NH | O | | | |
| 161 | 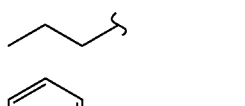 | O | O | H | H | CH₃ |
| 162 | | NH | O | | | |
| 163 | 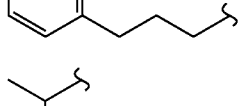 | O | O | H | H | CH₃ |
| 164 | | NH | O | | | |
| 165 | 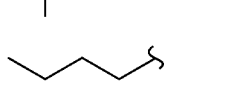 | O | O | H | H | CH₃ |
| 166 | | NH | O | | | |
| 167 | 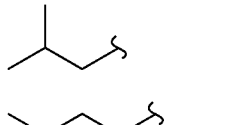 | O | O | H | H | CH₃ |
| 168 | | NH | O | | | |
| 169 |  | O | O | H | H | CH₃ |
| 170 | | NH | O | | | |
| 171 |  | O | O | H | H | CH₃ |
| 172 | | NH | O | | | |
| 173 |  | O | O | H | H | CH₃ |
| 174 | | NH | O | | | |

TABLE 2-continued

| Compd. No. | R⁷ | A | Y | R⁴ | R⁵ | R⁶ |
|---|---|---|---|---|---|---|
| 175 | pentyl | O | O | H | H | CH₃ |
| 176 | | NH | O | | | |
| 177 | hexyl | O | O | H | H | CH₃ |
| 178 | | NH | O | | | |
| 179 | octyl | O | O | H | H | CH₃ |
| 180 | | NH | O | | | |
| 181 | phenyl | O | O | H | H | CH₃ |
| 182 | | NH | O | | | |
| 183 | | NCH₃ | O | | | |
| 184 | | O | S | | | |
| 185 | | NH | S | | | |
| 186 | | NCH₃ | S | | | |
| 187 | phenyl | O | O | H | H | H |
| 188 | | NH | O | | | |
| 189 | phenyl | O | O | H | CH₃ | CH₃ |
| 190 | | NH | O | | | |
| 191 | phenyl | O | O | H | H | CH₂CH₃ |
| 192 | | NH | O | | | |
| 193 | phenyl | O | O | H | H | CH₂CH₂CH₃ |
| 194 | | NH | O | | | |
| 195 | phenyl | O | O | CH₃ | H | CH₃ |
| 196 | | NH | O | | | |
| 197 | naphthyl | O | O | H | H | CH₃ |
| 198 | | NH | O | | | |
| 199 | naphthyl | O | O | H | H | CH₃ |
| 200 | | NH | O | | | |
| 201 | 2-pyridyl | O | O | H | H | CH₃ |
| 202 | | NH | O | | | |
| 203 | 3-pyridyl | O | O | H | H | CH₃ |
| 204 | | NH | O | | | |

TABLE 2-continued
| Compd. No. | R[7] | A | Y | R[4] | R[5] | R[6] |
|---|---|---|---|---|---|---|
| 205 | 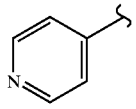 | O | O | H | H | CH$_3$ |
| 206 | | NH | O | | | |
| 207 | 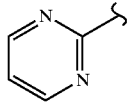 | O | O | H | H | CH$_3$ |
| 208 | | NH | O | | | |
| 209 | 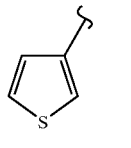 | O | O | H | H | CH$_3$ |
| 210 | | NH | O | | | |
| 211 | 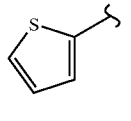 | O | O | H | H | CH$_3$ |
| 212 | | NH | O | | | |
| 213 | 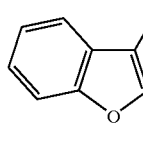 | O | O | H | H | CH$_3$ |
| 214 | | NH | O | | | |
| 215 | 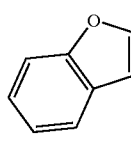 | O | O | H | H | CH$_3$ |
| 216 | | NH | O | | | |
| 217 | 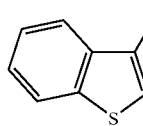 | O | O | H | H | CH$_3$ |
| 218 | | NH | O | | | |
| 219 | 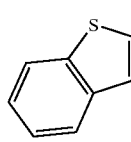 | O | O | H | H | CH$_3$ |
| 220 | | NH | O | | | |
| 221 | 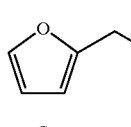 | O | O | H | H | CH$_3$ |
| 222 | | NH | O | | | |
| 223 | 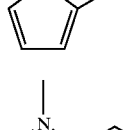 | O | O | H | H | CH$_3$ |
| 224 | | NH | O | | | |
| 225 | 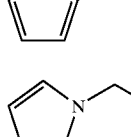 | O | O | H | H | CH$_3$ |
| 226 | | NH | O | | | |
| 227 |  | O | O | H | H | CH$_3$ |
| 228 | | NH | O | | | |

TABLE 2-continued

| Compd. No. | R⁷ | A | Y | R⁴ | R⁵ | R⁶ |
|---|---|---|---|---|---|---|
| 229 | (1-(2-methylimidazolyl)propyl) | O | O | H | H | $CH_3$ |
| 230 | | NH | O | | | |
| 231 | (4-nitroimidazolyl-propyl) | O | O | H | H | $CH_3$ |
| 232 | | NH | O | | | |
| 233 | (4-nitro-2-methylimidazolyl-propyl) | O | O | H | H | $CH_3$ |
| 234 | | NH | O | | | |
| 235 | (piperidinyl-propyl) | O | O | H | H | $CH_3$ |
| 236 | | NH | O | | | |
| 237 | (2-pyridyl-propyl) | O | O | H | H | $CH_3$ |
| 238 | | NH | O | | | |
| 239 | (4-pyridyl-propyl) | O | O | H | H | $CH_3$ |
| 240 | | NH | O | | | |

In view of the above, $R^5$ may represent hydrogen atom; and $R^6$ may represent a $C_1$–$C_2$ alkyl group which may optionally be substituted with a hydroxyl group, a hydroxyl group or a $C_1$–$C_2$ alkoxy group.

The amide derivatives of the present invention represented by the above general formula (I) wherein X is $R^1(R^2)(R^3)C$—, and Y is an oxygen atom, can be prepared by, for example, the method explained below.

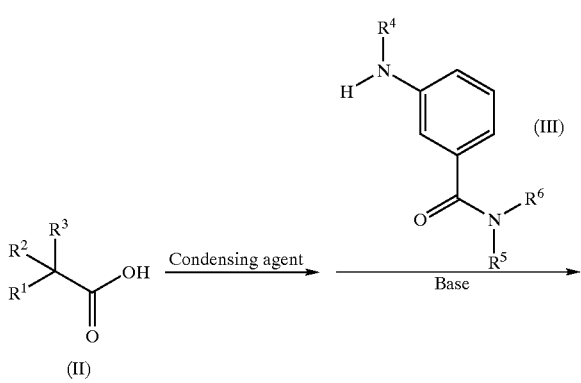

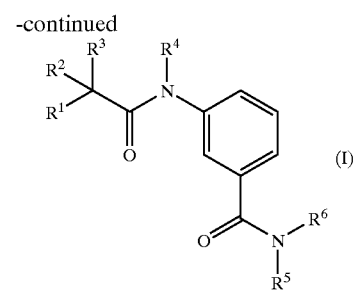

wherein $R^1$, $R^2$, $R^3$, $R^4$, $R^5$, and $R^6$ are the same as those defined above.

A carboxylic acid derivative represented by the above general formula (II) is allowed to react with a condensing agent such as dicyclohexylcarbodiimide, diphenylphospborylazide, carbonyldiimidazole, oxalyl chloride, isobutyl chloroformate, and thionyl chloride, optionally in the presence of a base such as triethylamine and pyridine as required, to activate a carboxylic acid, and then the resulting intermediate is allowed to react with an aniline derivative represented by the above general formula (III), optionally in the presence of a base such as triethylamine and pyridine as required, to obtain a compound represented by the above general formula (I). As a solvent used in the condensation reaction, a stable solvent may be appropriately chosen depending on a type of a condensing agent Reaction conditions may also be appropriately chosen so as to be suitable for a condensing agent used.

In the above series of reactions, protection and deprotection of one or more functional groups may sometimes be required. In such a case, 8 protective group suitable for each of the reactive functional group may be chosen, and reaction procedures can be employed according to known methods described in the literature.

The amide derivatives of the present invention represented by the above general formula (I) wherein X is $R^7$—A—, can be prepared by, for example, the method explained below.

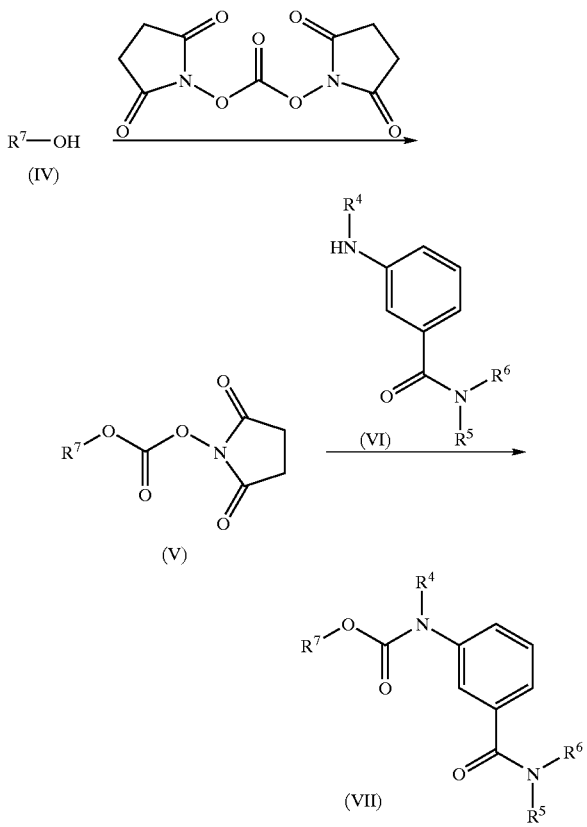

wherein $R^7$, $R^4$, $R^5$, and $R^6$ are the same as those defined above.

An alcohol derivative represented by the above general formula (IV) is dissolved in an inert solvent such as acetonitrile, methylene chloride or chloroform, and allowed to be reacted with di(n-succinmidyl)carbonate in the presence of base such as triethylamine or pyridine to obtain an asymmetric carbonate compound (V) as an intermediate. The compound (V) is then dissolved in a polar solvent such as dimethylformamide, N-methylpyrrolidone or dimethylsulfoxide, and allowed to be reacted with the aniline derivative (VI) in the presence of base such as triethylamine or pyridine to obtain the compound (VII), i.e., the compound represented by the formula (I) wherein A and Y are an oxygen atom.

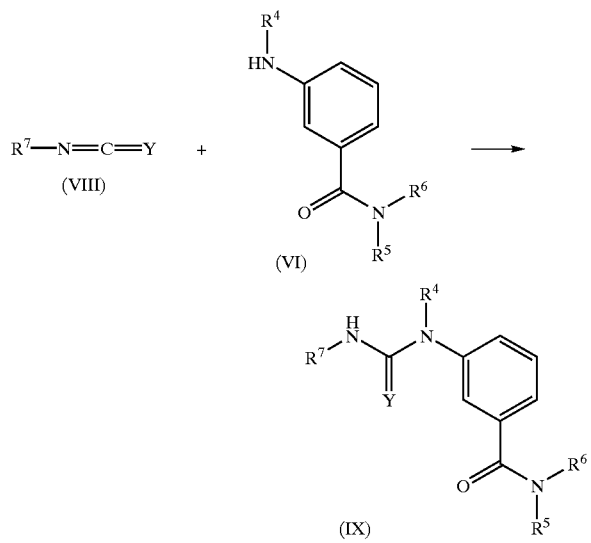

wherein $R^7$, $R^4$, $R^5$, $R^6$ and Y are the same as those defined above.

The isocyanate derivative (VIII) is dissolved in an inert solvent such as acetonitrile, methylene chloride or chloroform, and allowed to be reacted with the aniline derivative (VI) to obtain the compound (IX), i.e., the compound represented by the formula (I) wherein A is —NH.

In the above series of reactions, protection and deprotection of one or more functional groups may sometimes be required. In such a case, a protective group suitable for each of the reactive functional group may be chosen, and reaction procedures can be employed according to known methods described in the literature.

The compounds of the present invention represented by the above general formula (I) have excellent antibacterial activity against Helicobacter pylori, and they can exhibit potent antibacterial activity against Helicobacter pylori in stomach Accordingly, the medicaments of the present invention are useful for therapeutic and/or preventive treatment of various digestive diseases related to the infection caused by Helicobacter pylori, for example, a disease selected from the group consisting of gastritis, gastric ulcer, gastric cancer; gastric malignant lymphoma, MALT lymphoma, duodenal ulcer, and duodenal carcinoma. More specifically, the compounds may preferably be used as medicaments for therapeutic treatment of gastritis, gastric ulcer and duodenal ulcer; medicaments for preventive treatment of gastric ulcer, duodenal ulcer, gastric malignant lymphoma, gastric cancer, and duodenal carcinoma; and medicaments for preventive treatment of recurrence of gastric ulcer and duodenal ulcer.

As an active ingredient of the medicament of the present invention, one or more substances selected from the group consisting of the compound represented by the above general formula (I) and a pharmaceutically acceptable salt thereof, and a solvate thereof and a hydrate thereof can be used. The medicament of the present invention may preferably be provided in the form of a pharmaceutical composition comprising the above substance as an active ingredient and one or more pharmaceutically acceptable additives for pharmaceutical preparations. In the pharmaceutical compositions, a ratio of the active ingredient to the pharmaceutical additive may be about 1% by weight to about 90% by weight.

The medicament of the present invention may be administered as a pharmaceutical composition for oral administration such as granules, subtilized granules, powders, hard capsules, soft capsules, syrups, emulsions, suspensions, and liquid drugs, or administered as a pharmaceutical composition for parenteral administration such as injections for intravenous, intramuscular or subcutaneous administration, drip infusions, and suppositories. A preparation prepared as a powdery pharmaceul composition may be dissolved before use and used as an injection or a drip infusion.

Solid or liquid pharmaceutical additives may be used for preparation of the pharmaceutical compositions. The pharmaceutical additives may be either organic or inorganic materials. Examples of excipients used for manufacturing solid preparations include, for example, lactose, sucrose, starch, talc, cellulose, dextrin, china clay, and calcium carbonate. For the manufacture of liquid formulations for oral admintation such as emulsions, syrups, suspensions, and liquids, for example, ordinary inert diluents such as water and vegetable oils may be used. In addition to the inert diluents, auxiliaries such as, for example, moistening agents, suspending aids, sweetening agents, aromatics, colorants, preservatives and the like may be formulated. Liquid preparations may be filled in capsules after their preparation that are made of an absorbable material such as gelatin. Examples of solvents or su spending mediums used for the manufacture of pharmaceutical preparations for parenteral administration such as injections and suppositories include, for example, water, propylene glycol, polyethylene glycol, berzyl alcohol, ethyl oleate, lecithin and the like. Examples of base materials used for preparation of suppositories include, for example, cacao butter, emulsified cacao butter, lauric lipid, Witepsol and the like. Methods for manufacturing the pharmaceutical preparations are notparticularly limited, and any methods ordinarily used in the art may be employed.

A dose of the medicament oft he present invention may generally be from about 0.01 to 5,000 mg per day for an adult based on the weight of the compounds of the present invention. However, it is preferred to suitably increase or decreased depending on age. conditions, symptoms or other of a patient The daily dose may be administered once a day or twice to three times a day with suitable intervals, or alternatively, intermittently administered with intervals of several days. When used as an injection, a dose of the medicaments of the present invention may be about 0.001 to 100 mg per day for an adult based on the weight of the compounds of the present invention.

EXAMPLES

The present invention will be explained more specifically by referring to the following examples. However, the scope of the present invention is not limited to these examples.

Example 1

Preparation of N-(3-methylcarbamoylphenyl)-3-chlorophenylacetamide (Compound No. 17 in Table 1)

3-Chlorophenylacetic acid (192 mg) was dissolved in methylene chloride (8 ml), and oxalyl chloride (0.10 ml) and one drop of dimethylformamide were added to the solution. After stirring for 1 hour at room temperature, 3-aminobenzoylmethyide (167 mg) and pyridine (0.19 ml) were added to the reaction mixture, and then stirred at room temperature overnight. After the solvent was evaporated under reduced pressure, water (10 ml) and 2N aqueous hydrochloric acid (1 ml) were added to the residue, and the deposited crystals were collected by filtration and washed with water. These crystals were dried and added in ethyl acetate (6 ml), and then the mixture was heated under reflux for ten minutes. The mixture was cooled to room temperature, and the crystals were collected by filtration and washed with ethyl acetate to obtain the desired compound (233 mg, yield 68%).

Melting point; 165–166° C.; IR (KBr, cm$^{-1}$): 3324, 1642, 1593, 1555; NMR (DMSO-d$_6$, δ): 2.76 (d, J=4.5 Hz, 3H), 3.68(s, 2H), 7.26–7.42 (m, 5H), 7.48 (d, J=7.8 Hz, 1H), 7.74 (d, J=7.8 Hz, 1H), 8.02 (dd, J=1.8 Hz, 1.8 Hz, 1H), 8.36 (d, J=4.5 Hz, 1H), 10.31 (s, 1H).

In similar manners to the method of Example 1, compounds of Examples 2–50 were prepared. Their physico-chemical properties are set out below.

Example 2

Preparation of N-(3-Methylcarbamoylphenyl) cyclohexylacetamide (Compound No. 4 in Table 1)

Melting point: 183° C.; IR (KBr, cm$^{-1}$): 3293, 1657, 1640, 1588, 1535; NMR (DMSO-d$_6$, δ); 0.99 (m, 2H), 1.03–1.38 (m, 3H), 1.55–1.90 (m, 6H), 2.19 (d, J=7.0 Hz, 2H), 2.76 (d, J=4.5 Hz, 3H), 7.34 (dd, J=7.8 Hz, 7.8 Hz, 1H), 7.45 (d, J=7.8 Hz, 1H), 7.74 (d, J=7.8 Hz, 1H), 8.01 (s, 1H), 8.34 (d, J=4.5 Hz, 1H), 9.95 (s, 1H).

Example 3

Preparation of N-(3-Methylcarbamoylphenyl) phenylacetamide (Compound No. 7 in Table 1)

Melting point; 140–142° C.; NMR (DMSO-d$_6$, δ): 2.75 (d, J=4.5 Hz, 3H), 3.63 (s, 2H), 7.22–7.48 (m, 7H), 7.74 (m, 1H), 8.01 (s, 1H), 8.37 (d, J=4.5 Hz, 1H), 10.30 (s, 1H).

Example 4

Preparation of N-(3-Methylcarbamoylphenyl)-1-phenylcyclopentanecarboxamide (Compound No. 11 in Table 1)

Melting point: 147° C.; IR (KBr, cm$^{-1}$): 3339, 3275, 1638, 1586, 1557, 1528; NMR (DMSO-d$_6$, δ): 1.67 (m, 4H), 1.94 (m, 2H), 2.65 (m, 2H), 2.75 (d, J=4.5 Hz, 3H, 7.20–7.60 (m, 7H), 7.76 (d, J=7.2 Hz, 1H), 7.98 (s, 1H), 8.33 (d, J=4.5 Hz, 1H), 9.32 (s, 1H).

Example 5

Preparation of N-(3-Methylcarbamoylphenyl)-3-fluorophenylacetamide (Compound No. 14 in Table 1)

Melting point: 147–148° C.; IR (KBr, cm$^{-1}$): 3314, 1661, 1636, 1587, 1530; NMR (DMSO-d$_6$, δ): 2.76 (d, J=4.2 Hz, 3H), 3.69 (s, 2H), 7.08 (dd, J=5.7Hz, 5.7 Hz, 1H), 7.14 (d, J=7.5 Hz, 2H), 7.38 (m, 2H), 7.47 (d, J=8.1 Hz, 1H), 7.74 (d, J=8.1 Hz, 1H), 8.02 (s, 1H), 8.35 (d, J=4.2 Hz, 1H), 10.30 (s, 1H).

Example 6

Preparation of N-(3-Methylcarbamoylphenyl)-4-fluorophenylacetamide (Compound No. 15 in Table 1)

Melting point: 155–156° C.; IR (KBr, cm$^{-1}$): 3293, 1657, 1634, 1588, 1535, 1512; NMR (DMSO-d$_6$, δ): 2.76 (d, J=3.9 Hz, 3H), 3.65 (s, 2H), 7.15 (dd, J=9.0 Hz, 9.0Hz, 2H), 7.25–7.41 (m, 3H), 7.47 (d, J=7.5 Hz, 1H), 7.75 (d, J=8.1 Hz, 1H), 8.02 (s, 1H), 8.35 (d, J=3.9 Hz, 1H), 10.28 (s, 1H).

Example 7

Preparation of N-(3-Methylcarbamoylphenyl)-2-chlorophenylacetamide (Compound No. 16 in Table 1)

Melting point: 211–212° C.; IR (KBr, cm$^{-1}$): 3268, 1659, 1642, 1586, 1535; NMR (DMSO-d$_6$, δ): 2.77 (d, J=3.6 Hz, 3H), 3.85 (s, 2H), 7.25–7.55 (m, 6H), 7.74 (d, J=7.5 Hz, 1H), 8.04 (s, 1H), 8.36 (d, J=3.6 Hz, 1H, 10.34 (s, 1H).

Example 8

Preparation of N-(3-Methylcarbamoylphenyl)-4-chlorophenyltamide (Compound No. 18 in Table 1)

Melting point: 163–164° C.; IR (KBr, cm$^{-1}$): 3279, 1663, 1640, 1588, 1535; NMR (DMSO-d$_6$, δ): 2.76 (d, J=3.9 Hz, 3H), 3.66 (s, 2H), 7.35–7.42 (m, 5H), 7.47 (d, J=7.8 Hz, 1H), 7.75 (d, J=7.8 Hz, 1H), 8.02 (dd, J=1.5 Hz, 1.5 Hz, 1H), 8.36 (d, J=3.9 Hz, 1H), 10.30 (s, 1H).

Example 9

Preparation of N-(3-Carbamoylphenyl)-3-bromophenylacetamide (Compound No. 20 in Table 1)

Melting point: 202° C.; IR (KBr, cm$^{-1}$): 3378, 3295, 1659, 1624, 1586, 1534; NMR (DMSO-d$_6$, δ): 3.67 (s, 2H), 7.20–7.60 (m, 7H), 7.76 (d, J=9.3 Hz, 1H), 7.94 (s, 1H), 8.03 (s, 1H), 10.33 (s, 1H).

Example 10

Preparation of N-(3-Methylcarbamoylphenyl)-3-bromophenylacetamide (Compound No. 22 in Table 1)

Melting point: 176–178° C.; IR (KBr, cm$^{-1}$): 3324, 3254, 1642, 1591, 1554; NMR (DMSO-d$_6$, δ): 2.76 (d, J=4.5 Hz, 3H), 3.68 (s, 2H), 77.27–7.41 (m, 3H), 7.45–7.50 (m, 2H), 7.56 (s, 1H), 7.75 (d, J=8.0 Hz 1H), 8.03 (s, 1H), 8.42 (d, J=4.5 Hz, 1H) 10.35 (s, 1H).

Example 11

Preparation of N-(3-Dimethylcarbamoylphenyl-3-bromophenylacetamide (Compound No. 23 in Table 1)

Melting point 119–120° C.; IR (KBr, cm$^{-1}$): 1678, 1613, 1588, 1557; NMR (DMSO-d$_6$, δ): 2.90 (s, 3H), 2.96 (s, 3H), 3.68 (s, 2H), 7.06 (d, J=7.8 Hz, 1H), 7.25–7.41 (m, 3H), 7.47 (m, 1H), 7.53–7.60 (m, 2H), 7.68 (s, 1H, 10.30 (s, 1H).

Example 12

Preparation of N-(3-Ethylcarbamoylphenyl)-3-bromophenylaetamide (Compound No. 24 in Table 1)

Melting point: 155° C.; IR (KBr, cm$^{-1}$): 3329, 3268, 1665, 1640, 1549; NMR (DMSO-d$_6$, δ): 1.11 (t, J=6.9 Hz, 3H), 3.29 (m, 2H), 3.67 (s, 2H, 7.20–7.40 (m, 3H), 7.47 (d, J=8.1 Hz, 1H), 7.49 (d, J=8.1 Hz, 1H), 7.56 (s, 1H), 7.75 (d, J=8.4 Hz, 1H), 8.00 (s, 1H), 8.41 (t, J=5.1 Hz, 1H), 10.32 (s, 1H).

Example 13

Preparation of N-(3-(2-Hydroxyethyl)carbamoylphenyl)-3-bromophenylacetamide (Compound No. 28 in Table 1)

Melting point: 202° C.; IR (KBr, cm$^{-1}$): 3407, 3358, 3279, 1671, 1640, 1589, 1539; NMR (DMSO-d$_6$, δ): 3.26 (m, 2H), 3.47 (m, 2H), 3.65 (s, 2H), 4.67 (t, J=5.7 Hz, 1H), 7.20–7.60 (m, 6H), 7.73 (d, J=7.2 Hz, 1H), 7.99 (s, 1H), 8.32 (m, 1H), 10.28 (s, 1H).

Example 14

Preparation of N-(3-Hydroxycarbamoylphenyl)-3-bromophenylacetamide (Compound No. 29 in Table 1)

Melting point: 184–186° C. (decompoition); IR (KBr, cm$^{-1}$): 3314, 3231, 1663, 1632, 1582, 1535; NMR (DMSO-d$_6$, δ): 3.68(s, 2H), 7.25–7.60 m, 6H), 7.75 (d, J=6.9 Hz, 1H), 7.98 (s, 1H), 9.01 (s, 1H), 10.33 (s, 1H), 11.12 (s, 1H).

Example 15

Preparation of N-(Methoxycarbamoylphenyl)-3-bromophenylacetamide (Compound No. 30 in Table 1)

Melting point: 166° C.; IR (KBr, cm$^{-1}$): 3299, 3187, 1659, 1611, 1595, 1560; NMR (DMSO-d$_6$, δ): 3.69 (s, 5H), 7.22–7.60 (m, 6H), 7.77 (s, 1H), 8.00 (s, 1H), 10.37 (s, 1H), 11.69 (s, 1H).

Example 16

Preparation of N-(3-Methylcarbamoylphenyl)-4-bromophenylacetamide (Compound No. 33 in Table 1)

Melting point; 165–166° C.; IR (KBr, cm$^{-1}$): 3283, 1665, 1642, 1588, 1534; NMR DMSO-d$_6$, δ): 2.77 (d, J=4.5 Hz, 3H), 3.64 (s, 2H), 7.23–7.40 (m, 3H), 7.40–7.58 (m, 3H), 7.75 (d, J=7.8 Hz, 1H), 8.01 (s, 1H), 8.37 (d, J=4.5 Hz, 1H), 10.30 (s, 1H).

Example 17

Preparation of N-(3-Methylcarbamoylphenyl)-3-methylphenylacetamide (Compound No. 42 in Table 1)

Melting point: 131° C.; IR (KBr, cm$^{-1}$): 3299, 1659, 1634, 1586, 1530; NMR (DMSO-d$_6$, δ): 2.29 (s, 3H), 2.76 (d, J=4.5 H 3H), 3.60 (s, 2H), 7.06 (d, J=6.9 Hz, 1H), 7.09–7.22 (m, 3H), 7.36 (dd, J=7.8 Hz, 7.8 Hz, 1H), 7.47 (d, J=7.8 Hz, 1H), 7.75 (d, J=7.8 Hz, 1H), 8.02 (s, 1H), 8.35 (d, J=4.5 Hz, 1H), 10.26 (s, 1H).

Example 18

Preparation of N-(3-Methylcarbamoylphenyl)-4-methylphenylacetamide (Compound No. 43 in Table 1)

Melting point: 174–175° C.; IR (KBr, cm$^{-1}$): 3339, 3296, 1659, 1639, 1586, 1528; NMR (DMSO-d$_6$, δ): 2.27 (s, 3H), 2.76 (d, J=4.5 Hz, 3H), 3.59 (s, 2H), 7.12 (d, J=8.1 Hz, 2H), 7.22 (d, J=8.1 Hz, 2H), 7.36 (dd, J=7.8 Hz, 7.84 Hz), 7.47 (d, J=7.8 Hz, 1H), 7.55 (d, J=7.8 Hz, 1H), 8.01 (s, 1H), 8.35 (d, J=4.5 Hz, 1H), 10.24 (s, 1H).

Example 19

Preparation of N-(3-Methylcarbamoylphenyl)-3-methoxyphenylacetamide (Compound No. 59 in Table 1)

Melting point: 104–106° C.; NM (DMSO-$d_6$, δ): 2.76 (d, J=4.5 Hz, 3H), 3.60 (s, 2H), 3.73 (m, 3H), 6.81 (m, 1H), 6.89–6.92 (m, 2H), 7.23 (m, 2H), 7.36 (m, 1H), 7.47 (m, 1H), 7.76 (m, 1H), 8.02 (s, 1H), 8.38 (m, 1H), 10.28 (s, 1H).

Example 20

Preparation of N-(3-Methylcarbamoylpbenyl)-4-methoxyphenylacetamide (Compound No. 60 in Table 1)

Melting point: 155–157° C.; NMR (DMSO-$d_6$, δ): 2.75 (d, J=4.5 Hz 3H), 3.55 (s, 2H), 3.71 (s, 3H), 6.88 (d, J=8.8 Hz, 2H), 7.24 (d, J=8.8 Hz, 2H), 7.35 (m, 1H), 7.45 (d, J=7.8 Hz, 1H), 7.74 (d, J=7.8 Hz, 1H), 8.00 (s, 1H), 8.37 (m, 1H), 10.24 (s, 1H).

Example 21

Preparation of N-(3-Methylcarbamoylphenyl)-3,4-dimethoxyphenylacetamide (Compound No. 61 in Table 1)

NMR DMSO-$d_6$, δ): 2.75 (d, J=4.5 Hz, 3H), 3.55 (s, 2H), 3.71 (s, 3H), 3.73 (s, 3H), 6.82–6.94 (m, 3H), 7.35 (m, 1H), 7.46 (d, J=7.8 Hz, 1H), 7.75 (d, J=7.8 Hz, 1H), 8.00 (s, 1H), 8.37 (m, 1H), 10.22 (s, 1H).

Example 22

Preparation of N-(3-Methylcarbamoylphenyl)-3,5-dimethoxyphenylacetamide (Compound No. 62 in Table 1)

Melting point: 146–147° C.; IR (KBr, $cm^{-1}$): 3341, 3246, 1667, 1638, 1589, 1547; NMR DMSO-$d_6$, δ): 2.76 (d J=4.2 Hz, 3H), 3.56 (s, 2H), 3.73 (s, 6H), 6.39 (s, 1H), 6.51 (s, 2H), 7.36 (dd, J=7.8 Hz, 7.8 Hz 1H), 7.47 (d, J=7.8 Hz, 1H), 7.75 (d, J=7.8 Hz, 1H), 8.01 (s, 1H), 8.35 (d, J=4.2 Hz, 1H), 10.23 (s, 1H).

Example 23

Preparation of N-(3-Methylcarbamoylphenyl)-3,4,5-trimethoxyphenylacetamide (Compound No. 63 in Table 1)

Melting point: 81–82° C.; IR (KBr, $cm^{-1}$): 3304, 1642, 1589, 1554, 1508; NMR (DMSO-$_6$, δ): 2.76 (d, J=4.5 Hz, 3H), 3.57 (s, 2H), 3.63 (s, 3H), 3.77 (s, 6H), 6.66 (s, 2H), 7.39 (dd, J=7.8 Hz, 7.8 Hz, 1H), 7.47 (d, J=7.8 Hz, 1H), 7.76 (d, J=7.8 Hz, 1H, 8.03 (s, 1H), (s, 1H), 8.37 (d, J=4.5 Hz, 1H), 10.23 (s, 1H).

Example 24

Preparation of N-(3-Methylcarbamoylphenyl)-3-benzyloxyphenylacetamide (Compound No. 68 in Table 1)

Melting point: 150° C.; IR (KBr, $cm^{-1}$): 3302, 1661, 1634, 1586, 1530; NMR (DMSO-$d_6$, δ): 2.76 (d, J=4.5 Hz, 3H), 3.61 (s, 2H), 5.09 (s, 2H), 6.91 (dd, J=7.8 Hz, 7.8 Hz, 2H), 7.01 (s, 1H), 7.27 (dd, J=7.8 Hz, 7.8Hz, 1H), 7.25–7.52 (m, 7H), 7.74 (d, J=7.8 Hz, 1H), 8.02 (s, 1H), 8.36 (d, J=4.5 Hz, 1H), 10.27 (s, 1H).

Example 25

Preparation of N-(3-Carbamoylphenyl)-3-hydroxyphenylacetamide (Compound No. 71 in Table 1)

Melting point: 188–189° C.; NMR (DMSO-$d_6$, δ): 3.52 (s, 2H), 6.62 (m, 1H), 6.72–6.75 (m, 2H), 7.08 (m, 1H), 7.32–7.37 (m, 2H, 7.51 (d, J=6.9 Hz, 1H), 7.76 (d, J=7.8 Hz, 1H), 7.92 (s 1H), 8.02 (s, 1H), 9.34 (s, 1H), 10.25 (s, 1H).

Example 26

Preparation of N-(3-Methylcarbamoylphenyl)-3-hydroxyphenylacetamide (Compound No. 72 in Table 1)

Melting point: 163° C.; IR (KBr, $cm^{-1}$): 3333, 3293. 1676, 1640, 1588, 1562; NMR (DMSO-$d_6$, δ): 2.74 (d, J=4.2 Hz, 3H), 3.53 (s, 2H), 6.61 (d, J=7.2 Hz, 1H), 6.72 (d, J=7.2Hz, 1H), 6.74 (s, 1H), 7.08 (dd, J=7.2 Hz, 7.2Hz, 1H), 7.34 (dd, J=7.8 Hz, 7.8 Hz, 1H), 7.45 (d, J=7.8 Hz, 1H), 7.73 (d, J=7.8 Hz, 1H), 7.80 (s, 1H), 8.34 (d, J=4.2 Hz, 1H), 9.30 (s, 1H), 10.22 (s, 1H).

Example 27

Preparation of N-(3-Methylcarbamoylphenyl)-4-hydroxyphenylacetamide (Compound No. 73 in Table 1)

Melding point: 195–196° C.; IR (KBr, $cm^{-1}$): 3393, 3283, 1661, 1638, 1541, 1518; NMR (DMSO-$d_6$, δ): 2.73 (d, J=4.5 Hz, 3H), 3.48 (s, 2H), 6.68 (d, J=8.4 Hz, 2H), 7.10 (d, J=8.4 Hz, 2H), 7.33 (dd, J=7.8 Hz, 7.8 Hz, 1H), 7.43 (d, J=8.7 Hz, 1H), 7.72 (d, J=7.8 Hz, 1H), 7.98 (s, 1H), 8.32 (d, J=4.5 Hz, 1H), 9.20 (s, 1H), 10.14 (s, 1H).

Example 28

Preparation of N-(3-methylcarbonylphenyl)-3-nitrophenylatamide (Compound No. 74 in Table 1)

Melting point: 139° C.; IR (KBr, $cm^{-1}$): 3322, 3250, 1665, 1640, 1666, 1624; NMR (DMSO-$d_6$, δ): 2.76 (d, J=4.5 Hz, 3H), 3.86 (s, 2H), 7.37 (dd, J=7.8 Hz, 7.8 Hz, 1H), 7.49 (d, J=7.8 Hz, 1H), 7.64 (dd, J=8.1 Hz, 8.1 Hz, 1H), 7.75 (d, J=8.1 Hz, 1H), 7.80 (d, J=8.1 Hz, 1H), 8.03 (s, 1H), 8.13 (d, J=8.1 Hz, 1H), 8.24 (s, 1H), 8.37 (d, J=4.5 Hz, 1H), 10.39 (s, 1H).

Example 29

Preparation of N-(3-Methylcarbamoylphenyl)-4-nitrophenylacetamide (Compound No. 75 in Table 1)

Melting point: 148–151° C.; IR (KBr, $cm^{-1}$): 3277, 1663, 1640, 1588, 1522; NMR (DMSO-$d_6$, δ): 274 (d, J=4.2 Hz, 3H), 3.83 (s, 2H), 7.35 (dd, J=7.8 Hz, 7.8 Hz, 1H), 7.45 (m, 1H), 7.60 (d, J=8.7 Hz, 2H), 7.72 (d, J=8.4 Hz, 1H), 8.00 (s, 1H), 8.19 (d, J=8.7 Hz, 2H), 8.33 (d, J=4.2 Hz, 1H), 10.36 (s, 1H.

Example 30

Preparation of N-(3-Methylcarbamoylphenyl)-1-naphthylacetamide (Compound No. 113 in Table 1)

Melting point: 201–202° C.; IR (KBr, $cm^{-1}$): 3274, 1657, 1640, 1588, 1532; NMR (DMSO-$d_6$, δ): 2.75 (d, J=4.5 Hz, 3H, 4.16 (s, 2H), 7.36 (dd, J=8.1 Hz, 8.1 Hz, 1H), 7.40–7.60 (m, 5H), 7.74 (d, J=7.8 Hz, 1H), 7.84 (d, J=7.8 Hz, 1H), 7.97 (d, J=7.8 Hz, 1H), 8.03 (s, 1H), 8.35 (d, J=7.8 Hz, 1H), 8.37 (d, J=4.5 Hz, 1H), 10.44 (s, 1H).

Example 31

Preparation of N-(3-Methylcarbamoylphenyl)-2-naphthylacetnide (Compound No. 114 in Table 1)

Melting point: 175–176° C.; IR (KBr, cm$^{-1}$): 3393, 1655, 1634, 1588, 1530; NMR DMSO-d$_6$, δ): 2.76 (d, J=4.5 Hz, 3H), 3.83 (s, 2H), 7.37 (dd, J=7.8 Hz, 7.8 Hz, 1H), 7.40–7.55 (m, 4H), 7.77 (d, J=8.4 Hz, 1H), 7.81–7.96 (m, 4H), 8.04 (s, 1H), 8.36 (d, J=4.5 Hz, 1H), 10.37 (s, 1H).

Example 32

Preparation of N-(3-Methylcarbamoylphenyl-3-indolylacetamide (Compound No. 140 in Table 1)

Melting point: 168–169° C.; IR (KBr, cm$^{-1}$): 3382, 3287, 1655, 1636, 1588, 1565, 1528; NMR (DMSO-d$_6$, δ): 2.73 (d, J=4.5 Hz 3H), 3.72 (s, 2H), 6.96 (dd, J=7.5 Hz, 7.5 Hz, 1H), 7.05 (dd, J=7.8 Hz, 7.8 Hz, 1H), 7.24 (s, 1H), 7.27–7.38 (m, 2H), 7.43 (d, J=7.8 Hz, 1H), 7.59 (d, J=7.8 Hz, 1H, 7.75 (d, J=8.7 Hz, 1H), 8.00 (s, 1H), 8.32 (d, J=4.5 Hz, 1H), 10.18 (s, 1H), 10.88 (s, 1H).

Example 33

Preparation of N-(3-Methylcarbamoylphenyl)-3-benzothienylacetamide (Compound No. 146 in Table 1)

Melting point: 194° C.; IR (KBr, cm$^{-1}$): 3285, 1663, 1636, 1588, 1532; NMR (DMSO-d$_6$, δ): 2.75 (d, J=4.2 Hz, 3H), 3.94 (s, 2H), 7.32–7.53 (m, 4H), 7.61 (s, 1H), 7.76 (d, J=6.9 Hz, 1H), 7.91 (d, J=7.2 Hz, 1H), 7.98 (d, J=7.2 Hz, 1H), 8.04 (s, 1H), 8.35 (d, J=4.2 Hz, 1H), 10.40 (s, 1H).

Example 34

Preparation of N-(3-Methylcarbamoylphenyl)-4-benzothienylacetamide (Compound No. 148 in Table 1)

Melting point: 192° C.; IR (KBr, cm$^{-1}$): 3295, 1676, 1632, 1595, 1559; NMR (DMSO-d$_6$, δ): 2.76 (d, J=4.2 Hz, 3H), 4.03 (s, 2H), 7.30–7.41 (m, 3H), 7.47 (d, J=7.8 Hz, 1H), 7.65 (d, J=5.4 Hz, 1H), 7.75 (d, J=6.3 Hz, 1H), 7.77 (d, J=5.4 Hz, 1H), 7.91 (m, 1H), 8.02 (s, 1H), 8.35 (d, J=4.2 Hz, 1H), 10.39 (s, 1H).

Example 35

Preparation of N-(3-Methylcarbamoylphenyl)-2,2-dimethyl-2,3-dihydro-5-benzofuranylacetamide (Compound No. 157 in Table 1)

Melting point: 92–93° C.; IR (KBr, cm$^{-1}$): 3289, 1665, 1611, 1589, 1555; NMR (DMSO-d$_6$, δ): 1.39 (s, 6H), 1.53 (s, 6H), 2.75 (d, J=4.5 Hz, 3H), 2.99 (s, 2H), 6.65 (d, J=8.4 Hz, 1H), 7.05 (d, J=8.1 Hz, 1H), 7.18 (s, 1H), 7.34 (dd, J=7.8 Hz, 7.8 Hz, 1H), 7.45 (d, J=7.5 Hz, 1H), 7.80 (d, J=7.8 Hz, 1H), 8.02 (s, 1H), 8.33 (d, J=4.5 H, 1H), 9.18 (s, 1H).

Example 36

Preparation of N-(3-Methylcarbamoylphenyl)-3,4-methylenedioxyphenyl-acetamide (Compound No. 159 in Table 1)

Melting point: 174–175° C.; IR (KBr, cm$^{-1}$): 3337, 3291, 1659, 1634, 1586, 1530, 1505; NMR (DMSO-d$_6$, δ): 2.76 (d, J=4.5 Hz, 3H), 3.55 (s, 2H), 5.98 (s, 2H), 6.74–6.93 (m, 3H), 7.36 (dd, J=7.8 Hz, 7.8 Hz, 1H), 7.47 (d, J=7.8 Hz, 1H), 7.75 (d, J=7.8 Hz 1H), 8.01 (s, 1H), 8.35 (d, J=4.5 Hz, 1H), 10.20 (s, 1H).

Example 37

Preparation of N-(3-Methylearbamoylphenyl) phenoxyacetaride (Compound No. 176 in Table 1)

Melting point: 131° C.; IR (KBr, cm$^{-1}$): 3378, 3283, 1669, 1640, 1588, 1535; NMR (DMSO-d$_6$, δ): 2.75 (d, J=4.5 Hz, 3H), 4.69 (s, 2H), 6.63–7.01 (m, 3H), 7.22–7.40 (m, 3H), 7.50 (d, J=7.8 Hz, 1H), 7.77 (d, J=7.8 Hz, 1H), 8.05 (s, 1H), 8.36 (d, J=4.5 Hz, 1H), 10.18 (s, 1H).

Example 38

Preparation of N-(3-Methylcarbamoylphenyl)-2-chlorophenoxyacetamide (Compound No. 177 in Table 1)

Melting point: 172–173° C.; IR (KBr, cm$^{-1}$): 3385, 3297, 1688, 1640, 1591, 1549; NMR (DMSO-d$_6$, δ): 2.77 (d, J=4.5 Hz, 3H), 4.85 (s, 2H), 6.99 (dd, J=7.5 Hz, 7.5 Hz, 1H), 7.08 (d, J=8.1 Hz, 1H), 7.30 (dd, J=7.5 Hz, 7.5 Hz, 1H), 7.38–7.60 (m, 3H), 7.76 (d, J=8.4 Hz, 1H), 8.06 (s, 1H), 8.42 (d, J=4.5 Hz, 1H), 10.31 (s, 1H).

Example 39

Preparation of N-(3-Methylcarbamoylphenyl)-2-methylphenoxyacetamide (Compound No. 183 in Table 1)

Melting point: 148° C.; IR (KBr, cm$^{-1}$): 3399, 3285, 1656, 1640, 1547; NMR (DMSO-d$_6$, δ): 2.24 (s, 3H), 2.75 (d, J=4.5 Hz, 3H), 4.70 (s, 2H), 6.80–6.90 (m, 2H), 7.07–7.19 (m, 2H), 7.37 (dd, J=8.1 Hz, 7.8 Hz, 1H), 7.49 (d, J=7.8 Hz, 1H), 7.75 (d, J=8.1 Hz, 1H), 8.05 (s, 1H), 8.35 (d, J=4.5 Hz, 1H), 10.14 (s, 1H).

Example 40

Preparation of N-(3-Methylcarbamoylphenyl)-2-methoxyphenoxyacetamide (Compound No. 187 in Table 1)

Melting point: 133° C.; IR (KBr, cm$^{-1}$): 3385, 3268, 1690, 1638, 1591, 1547; NMR (DMSO-d$_6$, δ): 2.75 (d, J=4.5 Hz, 3H), 3,79 (s, 3H), 4.66 (s, 2H), 6.82–7.02 (m, 4H), 7.38 (dd, J=7.8 Hz, 7.8 Hz, 1H), 7.49 (d, J=7.8 Hz, 1H, 7.75 (d, J=7.8 Hz, 1H, 8.05 (s, 1H), 8.38 (d, J=4.5 Hz, 1H), 10.18 (s, 1H).

Example 41

Preparation of N-(3-Methylcarbamoylphenyl)-1-naphthyloxyacetamide (Compound No. 191 Table 1)

Melting point: 194° C.; IR (KBr, cm$^{-1}$): 3405, 3304, 1696, 1638, 1541; NMR (DMSO-$_6$, δ): 2.75 (d, J=4.2 Hz, 3H), 4.92 (s, 2H, 6.92 (d, J=7.8 Hz, 1H), 7.33–7.62 (m, 6H), 7.79 (d, J=8.1 Hz, 1H), 7.88 (m, 1H), 8.08 (s, 1H), 8.31 (m, 1H), 8.41 (d, J=4.2 Hz, 1H), 10.36 (s, 1H).

Example 42

Preparation of N-(3-Methylcarbamoylphenyl)-2-naphthyloxyacetamide (Compound No. 192 in Table 1)

Melting point: 174° C.; IR (KBr, cm$^{-1}$): 3382, 3275, 1672, 1638, 1588, 1557, 1534; NMR (DMSO-d$_6$, δ): 2.75 (d, J=4.5 Hz, 3H), 4.82 (s, 2H), 7.22–7.58 (m, 6H), 7.78–7.95 (m, 4H), 8.09 (s, 1H), 8.40 (d, J=4.5 Hz, 1H), 10.28 (s, 1H).

Example 43

Preparation of N-(3-Methylcarbamoylphenyl)-2,3-dichlorophenoxyacetamide (Compound No. 204 in Table 1)

Melting point: 192–193° C.; IR (KBr, cm$^{-1}$): 3385, 3291, 1692, 1644, 1547; NMR (DMSO-d$_6$, δ): 2.77 (d, J=4.5 Hz 3H), 4.91 (s 2H), 7.08 (d, J=8.1 H, 1H), 7.20–7.45 (m, 3H), 7.52 (d, J=7.8 Hz, 1H), 7.74 (d, J=8.7 Hz, 1H), 8.05 (s, 1H), 8.42 (d, J=4.5 Hz, 1H), 10.34 (s, 1H).

Example 44

Preparation of N-(3-Methylcarbamoylphenyl)-2-methyl-1-naphthylacetamide (Compound No. 216 in Table 1)

Melting point: 230–231° C.; IR (KBr, cm$^{-1}$): 3299, 3071, 1684, 1638, 1589, 1560; NMR (DMSO-d$_6$, δ): 2.50 (s, 3H), 2.73 (d, J=4.5 Hz, 3H), 4.21 (s, 2H), 7.22–7.55 (m, 5H), 7.65–7.78 (m, 2H), 7.85 (d, J=7.8 Hz, 1H), 8.01–8.15 (m, 2H), 8.36 (d, J=4.5 Hz, 1H), 10.50 (s, 1H),

Example 45

Preparation of N-(3-Methylcarbamoylphenyl)-2-hydroxy-1-naphthylacetamide (Compound No. 219 in Table 1)

Melting point: 229–230° C.; IR (KBr, cm$^{-1}$): 3310, 1686, 1613, 1582, 1661; NMR (DMSO-d$_6$, δ): 2.75 (d, J=4.2 Hz, 3H), 4.11 (s, 2H), 7.19 (d, J=9.0 Hz, 1H), 7.20–7.50 (m, 4H), 7.66–7.82 (m, 3H), 7.87 (d, J=8.4 Hz, 1H), 8.04 (s, 1H), 8.37 (d, J=4.5 Hz, 1H), 9.79 (s, 1), 10.32 (s, 1H).

Example 46

Preparation of N-(3-Methylcarbamoylphenyl)-3-phenylpropionamide (Compound No. 233 in Table 1)

Melting point; 142–143° C.; IR (KBr, cm$^{-1}$): 3295, 1657, 1613, 1593, 1545; NMR (DMSO-d$_6$, δ): 2.62 (t, J=7.8 Hz, 2H), 2.75 (d, J=4.5 Hz, 3H), 2.90 (t, J=7.8 Hz, 2H), 7.10–7.40 (m, 6H), 7.44 (d, J=7.5 Hz, 1H), 7.72 (d, J=7.5 Hz, 1H), 7.99 (s, 1H), 8.33 (d, 4.5 Hz, 1H), 10.00 (s, 1H).

Example 47

Preparation of N-(3-Methylcarbamoylphenyl)-3-(2-methylphenyl)propionamide (Compound No. 240 in Table 1)

Melting point: 131° C.; IR (KBr, cm$^{-1}$): 3289, 1674, 1640, 1555; NMR (DMSO-d$_6$, δ): 2.29 (s, 3H, 2.57 (t, J=7.8 Hz, 2H), 2.75 (d, J=4.2 Hz, 3H), 2.88 (t, J=7.8 Hz, 2H), 7.02–7.18 (m, 4H), 7.34 (dd, J=7.8 Hz, 7.2 Hz, 1H), 7.44 (d, J=7.2 Hz, 1H), 7.73 (d, J=7.8 Hz, 1H), 7.98 (s, 1H), 8.33 (d, J=4.2 Hz 1H), 10.01 (s, 1H).

Example 48

Preparation of N-(3-Methylcarbamoylphenyl)-3-(4-hydroxyphenyl)propionamide (Compound No. 246 in Table 1)

Melting point: 158° C.; IR (KBr, cm$^{-1}$): 3424, 3285, 1647, 1553; NMR (DMSO-d$_6$, δ): 2.54 (t J=7.8 Hz, 2H), 2.74 (d, J=4.2 Hz 3H), 2.78 (t, J=7.8 Hz, 2H), 6.64 (d, J=8.1 Hz, 2H), 7.01 (d, J=8.1 Hz, 2H), 7.33 (dd, J=8.1 Hz, 7.5 Hz, 1H), 7.43 (d, J=7.5 Hz, 1H), 7.71 (d, J=8.1 Hz, 1H), 7.98 (s, 1H, 8.32 (d, J=4.2 Hz, 1H), 9.10 (s, 1H), 9.97 (s, 1H).

Example 49

Preparation of N-(3-Methylcarbamoylphenyl)-3-(2-methoxyphenyl)propienamide (Compound No. 246 in Table 1)

Melting point: 150° C.; IR (KBr, cm$^{-1}$): 3297, 1658, 1644, 1550; NMR (DMSO-d$_6$, δ): 2.56 (t, J=7.2 Hz, 2H), 2.75 (d, J=3.9 Hz, 3H), 2.85 (t, J=7.2 Hz, 2H), 3.78 (s, 3H), 6.84 (dd, J=7.5 Hz, 7.5 Hz, 1H), 6.93 (d, J=7.5 Hz, 1H), 7.05–7.20 (m, 2H), 7.26 (dd, J=8.1 Hz, 8.1 Hz, 1H), 7.34 (d, J=8.1 Hz, 1H), 7.72 (d, J=8.1 Hz, 1H), 7.99 (s, 1H), 8.38 (d, J=3.9 Hz, 1H), 9.67 (s, 1H).

Example 50

Preparation of N-(3-Methylcarbamoylphenyl)-3-(4-methoxyphenyl)propionamide (Compound No. 248 in Table 1)

Melting point: 151–152° C.; IR (KBr, cm$^{-1}$): 3289, 1669, 1634, 1613, 1557, 1514; NMR (DMSO-d$_6$, δ): 2.57 (t J=7.5 Hz, 2H), 2.77 (d, J=4.2 Hz, 3H), 2.85 (t, J=7.5 Hz, 2H), 3.71 (s, 3H), 6.84 (d, J=8.1 Hz, 2H), 7.16 (d, J=8.1 Hz, 2H), 7.35 (dd, J=7.8 Hz, 7.8 Hz, 1H), 7.45 (d, J=7.8 Hz, 1H), 7.74 (d. J=7.5 Hz, 1H), 8.01 (s, 1H), 8.34 (d, J=4.2 Hz, 1H), 10.00 (s, 1H).

Example 51

Preparation of N'-Methyl-3-(4-methylbenzyloxycarbonylamino)benzamide (Compound No. 51 in Table 2)

4-Methylbenzylalcohol (307 mg) and di(N-succinimidyl) carbonate (966mg) were dissolved in methylene chloride (20 ml), and triethylamine (0.70 ml) was added to the solution. After stirring for 4 hours at room temperature, water was added and an aqueous layer was extracted with methylne chloride. The extracted aqueous layer was successively washed with an aqueous saturated sodium chloride solution, an aqueous saturated sodium bicarbonate solution, an aqueous saturated sodium chloride solution, 2N hydrcroric acid, and an aqueous saturated sodium chloride solution, and dried over magnesia sulfite. After removing magnesium sulfate by titration, the filtrate was concentrated to obtain N-(4-methylbenzyloxycarbonyloxy)succinate imide (664 mg) as an intermediate.

N-(4-methylbenzyloxycarbonyloxy)succinate imide (610 mg of the above-obtained product) was dissolved in dimethylformanmide (2 ml), and 3-aminobenzoylmethylamide (313 mg) and triethylamine (0.32 ml) were added thereto. After stirring overnight at room temperature, the obtained insoluble material was added to water (15 ml) while the insoluble products are being filtered. The crystals obtained from filtrate was filtered and washed with water to obtain crude crystals. The crude crystals were dried and added to ethyl acetate (8 ml), and was heated under reflux for 10 minutes. The mixture was cooled to room temperature, and the crystals were collected by filtration and washed with ethyl acetate to obtain the desired compound (167 mg, yield 27%).

Melting Point: 167–168° C.; IR(KBr, cm$^{-1}$): 3322, 1738, 1622, 1557; NMR(DMSO-d$_6$, δ): 2.28(s, 3H), 2.74(d, J=4.6

Hz, 3H), 5.09(s, 2H), 7.17(d, J=7.9 Hz, 2H), 7.23–7.42(m, 4H), 7.54(d, J=6.5 Hz, 1H), 7.91(s, 1H), 8.31(d, J=4.61 Hz, 1H), 9.82(s, 1H).

In similar manners to the method of Example 51, compounds of Example 52–68 and Example 72 were prepared. Their physicochemical propertes are set out below.

Example 52

Preparation of N'-Methyl-3-(2-fluorobenzyloxycarbonylamino)benzamide (Compound No. 17 in Table 2)

Melting Point: 189–190° C.; IR(KBr, cm$^{-1}$): 3341, 3291, 1730, 1622, 1557; NMR(DMSO-d$_6$, δ): 2.76(d, J=4.2 Hz, 3H), 5.22(s, 2H), 7.20–7.45(m, 5H), 7.50–7.60(m, 2H), 7.94(s, 1H), 8.36(d, J=4.2 Hz, 1H), 9.53(s, 1H).

Example 53

Preparation of N'-Methyl-3-(4-fluorobenzyloxycarbonylamino)benzamide (Compound No. 21 in Table 2)

Melting Point: 153° C.; IR(KBr, cm$^{-1}$): 3304, 1732, 1626, 1613, 1559; NMR(DMSO-d$_6$, δ): 2.76(d, J=3.4 Hz, 3H), 5.15(s, 2H), 7.23(dd, J=8.6 Hz, 8.6 Hz, 2H), 7.35(dd, J=7.7 Hz, 7.4 Hz, 1H), 7.42(d, J=7.4 Hz, 1H), 7.49(dd, J=8.6 Hz, 8.6 Hz, 2H), 7.57(d, J=7.7 Hz 1H), 7.94(s, 1H), 8.36(d, J=3.4 Hz, 1H), 9.90(s, 1H).

Example 54

Preparation of N'-Methyl-3-(2-chlorobenzyloxycarbonylamino)benzamide (Compound No. 23 in Table 2)

Melting Point: 168° C.; IR(KBr, cm$^{-1}$): 3329, 3289, 1728, 1622, 1559; NMR(DMSO-d$_6$, δ): 2.74(d, J=4.4 Hz, 3H), 5.23(s, 2H), 7.27–7.43(m, 4H), 7.43–7.60(m, 3H), 7.93(s, 1H), 8.30(d, J=4.4 Hz, 1H), 9.94(s, 1H).

Example 56

Preparation of N'-Methyl-3-(4-chlorobenzyloxycarbonylamino)benzamide (Compound No. 27 in Table 2)

Melting Point: 155–156° C.; IR(KBr, cm$^{-1}$): 3351, 3299, 1734, 1624, 1557; NMR(DMSO-d$_6$, δ): 2.74(d, J=4.5 Hz, 3H), 5.14(s, 2H), 7.25–7.43(m, 6H), 7.55(d, J=8.3 Hz, 1H), 7.91(s, 1H), 8.32(d, J=4.5 Hz, 1H), 9.88(s, 1H).

Example 56

Preparation of N'-Methyl-3-(2,3-dichlorobenzyloxycarbonylamino)benzamide (Compound No. 29 in Table 2)

Melting Point: 167–168° C.; IR(KBr, cm$^{-1}$): 3401, 3258, 1744, 1711, 1649, 1561; NMR(DMSO-d$_6$, δ): 2.74(d, J=4.4 Hz, 3H), 5.26(s, 2H), 7.25–7.43(m, 3H), 7.50–7.60(m, 2H), 7.64(d, J8.0 Hz, 1H), 7.93(s, 1H), 8.32(d, J=4.4 Hz, 1H), 9.97(s, 1H).

Example 57

Preparation of N'-Methyl-3-(2,6-dichlorobenzyloxycarbonylamino)benzamide (Compound No. 35 in Table 2)

Melting Point: 219–220° C.; IR(KBr, cm$^{-1}$): 3380, 3241, 1717, 1651, 1562; NMR(DMSO-d$_6$, δ): 2.74(d, J=4.3 Hz, 3H), 5.35(s, 2H), 7.25–7.60(m, 6H), 7.92(s, 1H), 8.35(d, J=4.3 Hz, 1H), 9.92(s, 1H).

Example 58

Preparation of N'-Methyl-3-(2-bromobenzyloxycarbonylamino)bezamide (Compound No. 41 in Table 2)

Melting Point: 163–164° C.; IR(KBr, cm$^{-1}$): 3324, 1728, 1622, 1559; NMR(DMSO-d$_6$, δ): 2.73(d, J=4.0 Hz, 3H), 5.19(s, 2H), 7.24–7.75(m, 7H), 7.93(s, 1H), 8.35(d, J=4.0 Hz, 1H), 9.98(s, 1H).

Example 59

Preparation of N'-Methyl-3-(2-methylbenzyloxycarbonylamio)benzamide (Compound No. 47 in Table 2)

Melting Point: 163° C.; IR(KBr, cm$^{-1}$): 3358, 3312, 1734, 1622, 1557; NMR(DMSO-d$_6$, δ): 2.35(s, 3H), 2.76(d, J=4.4 Hz, 3H), 5.17(s, 2H), 7.18–7.35(m, 3H), 7.35–7.45(m, 3H), 7.57(d, J=7.7 Hz, 1H), 7.94(s, 1H), 8.37(d, J=4.4 Hz, 1H), 9.89(s, 1H).

Example 60

Preparation of N'-Methyl-3-(3-methylbenzyloxycarbonylamino)benzamide (Compound No. 49 in Table 2)

Melting Point: 155° C.; IR(KBr, cm$^{-1}$): 3343, 3279, 1736, 1624, 1559; NMR(DMSO-d$_6$, δ): 2.32(s, 3H), 2.76(d, J=4.2 Hz, 3H), 5.12(s, 2H), 7.10–7.45(m, 6H), 7.57(d, J=8.0 Hz, 1H), 7.94(s, 1H), 8.36(d, J=4.2 Hz, 1H), 9.89(s, 1H).

Example 61

Preparation of N'-Methyl-3-(4-isopxopylbenzyloxycarbonylamino)benzamide (Compound No. 57 in Table 2)

Melting Point: 189–190° C.; IR(KBr, cm$^{-1}$): 3380, 3235, 1709, 1647, 1561; NMR(DMSO-d$_6$, δ): 1.19(d, J=6.8 Hz, 6H), 2.76(d, J=3.9 Hz, 3H), 2.88(m, 1H), 5.12(s, 2H), 7.20–7.40(m, 6H), 7.57(d, J=7.7 Hz, 1H), 7.93(s, 1H), 8.35(d, J=3.9 Hz, 1H), 9.87(s, 1H).

Example 62

Preparation of N'-Methyl-3-(2-methoxybenzytoxycarbonylamino)benzamide (Compound No. 61 in Table 2)

Melting Point: 173° C.; IR(KBr, cm$^{-1}$): 3341, 3266, 1726, 1624, 1561; NMR(DMSO-d$_6$, δ): 2.76(d, J=4.0 Hz, 3H), 3.82(s, 3H), 5.14(s, 2H), 6.99(dd, J=7.4 Hz, 1H), 7.04(d, J=8.2 Hz, 1H), 7.28–7.42(m, 4H), 7.56(d, J=8.2 Hz, 1H), 7.94(s, 1H), 8.36(d, J=4.0 Hz, 1H), 9.89(s, 1H).

Example 63

Preparation of N'-Methyl-3-(4-methoxybenzyloxycarbonylamino)benzamide (Compound No. 65 in Table 2)

Melting Point: 158–159° C.; IR(KBr, cm$^{-1}$): 3331, 3295, 1730, 1613, 1555; NMR(DMSO-d$_6$, δ): 2.74(d, J=4.3 Hz, 3H), 3.73(s, 3H), 5.06(s, 2H), 6.92(d, J=8.2 Hz, 2H, 7.20–7.40(m, 4H), 7.54(d, J=7.7 Hz, 1M), 7.90(s, 1H), 8.30(d, J=4.3 Hz, 1H), 9.78(s, 1H).

Example 64

Preparation of N'-Methyl-3-(4-chloro2-nitrobenzyloxycarbonylamino)benzamide (Compound No. 77 in Table 2)

Melting Point: 193° C.; IR(KBr, cm$^{-1}$): 3366, 3248, 1717, 1624, 1662, 1537; NMR(DMSO-d$_6$, δ): 2.76(d, J=3.3 Hz, 3H), 5.48(s, 2H), 7.36(dd, J=7.8 Hz, 7.8 Hz, 1H), 7.44 (d, J=7.8 Hz, 1H), 7.58(d, J=7.8 Hz, 1H), 7.77(d, J=8.1 Hz, 1H), 7.90–7.98(m, 2H), 8.23(s, 1H), 8.35(d, J=3.3 Hz, 1H), 10.04(s, 1H).

Example 65

Preparation of N'-Methyl-3-(1-naphthylmethoxycarbonylamino)benzamide (Compound No. 81 in Table 2)

Melting Point: 228–229° C.; IR(KBr, cm$^{-1}$): 3353, 3285, 1730, 1626, 1555; NMR(DMSO-d$_6$, δ): 2.76(d, J=4.4 Hz, 3H), 5.64(s, 2H), 7.30–7.45(m, 2H), 7.50–7.70(m, 5H), 7.90–8.03(m, 3H), 8.12(d, J=7.6 Hz, 1H), 8.38(d, J=4.4 Hz, 1H), 9.87(s, 1H).

Example 66

Preparation of N'-Methyl-3-(2-naphthylmethoxycarbonylamino)benzamide (Compound No. 89 in Table 2)

Melting Point: 157–158° C.; IR(KBr, cm$^{-1}$): 3314, 1699, 1642, 1589, 1539; NMR(DMSO-$_6$, δ): 2.76(d, J=4.8 Hz, 3H), 5.32(s, 2H), 7.23–7.42(m, 2H), 7.42–7.60(m,4H), 7.82–7.98(m, 5H), 8.32(d, J=4.8 Hz, 1H), 9.90(s, 1H).

Example 67

Preparation of N'-Methyl-3-(5-fluorenylmethoxycarbonylamio)benzamide (Compound No. 99 in Table 2)

Melting Point: 217° C.; IR(KBr, cm$^{-1}$): 3349, 3289, 1730, 1624, 1586, 1557; NMR(DMSO-d$_6$, δ): 2.76(d, J=4.2Hz, 3H), 4,32(t, J=6.6 Hz, 1H), 4.48(d, J=6.6 Hz, 2H), 7.25–7.50 (m, 6H), 7.59(m, 1H), 7.76(d, J=7.2 Hz, 2H, 7.92(d, J=7.2 Hz, 2H), 7.93(s, 1H), 8.37(d, J=4.2 Hz, 1H), 9.87(s, 1H).

Example 68

Preparation of N'-Methyl-3-(phenoxycarbonylamino)benzamide(Compound No. 181 in Table 2)

Melting Point: 193° C.; IR(KBr, cm$^{-1}$): 3401, 3268, 1763, 1624, 1555; NMR(DMSO-d$_6$, δ): 2.77(d, J=3.6 Hz, 3H), 7.20–7.35(m, 3H), 7.35–7.45(m, 4H), 7.49(d, J=7.8 Hz, 1H), 7.63(s, 1H), 7.99(s, 1H), 10.38(s, 1H).

Example 69

Preparation of 1-(3-Methylcarbamoylphenyl)-3-phenylurea(Compound No. 182 in Table 2)

Phenylisocyanate (209 mg) and 3-aminobenzoylmethylamide (239 mg) were dissolved in dimethylformamide (2 ml). After starring for 6 hours at room temperature, dilute hydrochloric acid (15 ml) was added. The obtained crystals were filtered and washed with water to obtain crude crystals. The crude crystals were dried under reduced pressure and added to ethyl acetate (8 ml), and the mixture was heated under reflux for 10 minutes. The mixture was cooled to room temperature, and the crystals were collected by filtration and washed with ethyl acetate to obtain the desired compound (386 mg, yield 90%).

Melting Point: 209–210° C.; IR(KBr, cm$^{-1}$): 3328, 3279, 1699, 1626, 1557; NMR(DMSO-d$_6$, δ): 2.75(d, J=4.1 Hz, 3H), 6.95(dd, J-7.3 Hz, 7.3 Hz, 1H), 7.20–7.45(m, 6H), 7.57(d, J=7.7 Hz, 1H), 7.86(s, 1H), 8.37(d, J=4.1 Hz, 1H), 8.67(s, 1H), 8.79(s, 1H).

In similar manners to the method of Example 69, compounds of Example 70 and Example 71 were prepared. Their physicochemical properties are set out below.

Example 70

Preparation of 3-Benzyl-1-(3-methylcarbamoylphenyl)urea(Compound No. 5 in Table 2)

Melting Point: 189–190° C.; IR(KBr, cm$^{-1}$): 3366, 3333, 1640, 1559; NMR(DMSO-d$_6$, δ): 2.73(d, J=4.4 Hz, 3H), 4.28(d, J=5.9 Hz, 2H), 6.62(t, J=5.9 Hz, 1H), 7.15–7.40(m, 7H), 7.54(d, J=7.3 Hz, 1H), 7.79(s, 1H), 8.28(d, J=4.4 Hz, 1H), 8.66(s, 1H).

Example 71

Preparation of 3-Benzyl-1-(3-methylcarbamoylphenyl)thiourca(Compound No. 6 in Table 2)

Melting Point: 199° C.; IR(KBr, cm$^{-1}$): 3343, 3246, 3069, 1630, 1584, 1528; NMR(DMSO-d$_6$, δ): 2.76(d, J=4.5 Hz, 3H), 4.72(d, J=5.4 Hz, 2H), 7.20–7.40(m, 6H), 7.45–7.60(m, 2H), 7.81(s, 1H), 8.20(s, 1H), 8.36(d, J=4.5 Hz, 1H), 9.65(s, 1H).

Example 72

Preparation of N'-Methyl-3-(2-(2methyl-5-nitro-1-imidazolyl) ethoxycarbonylamino)benzamide (Compound No. 233 in Table 2)

Melting Point: 207° C.; IR(KBr, cm$^{-1}$): 3362, 1734, 1636, 1591, 1533; NMR(DMSO-d$_6$, δ): 2.48(s, 3H), 2.76(d, J=4.2 Hz, 3H), 4.47(t, J=4.8 Hz, 2H), 4.61(t, J=4.8 Hz, 2H), 7.34(dd, J=7.7 Hz, 7.5 Hz, 1H), 7.43(d, J=7.5 Hz, 1H), 7.55(d, J=7.7 Hz, 1H), 7.85(s, 1H), 8.05(s, 1H), 8.34(d, J=4.4 Hz, 1H), 9.76(s, 1H)

Test Example 1

Measurement of Anti-Helicobacter Pylori Activity

Brain heart infusion culture medium containing 10% fetal bovine serum (Difco) (5 ml) was taken in a test tube, and then the medium was inoculated with Helicobacter pylori strain 31A isolated from human (obtained from the Metropolitan Health Institute, Microorganism Department, First Laboratory of Bacteria). Cultivation was carried out under slightly aerobic condition (5% oxygen, 10% carbon dioxide, 85% nitrogen) at 37° C. for 48 hours with shaking.

The culture was then inoculated to brain heart infusion medium containing 10% fetal bovine serum at a ratio of 5%, and added with a test compound dissolved in 10% dimethyl sulfoxide. Cultivation was carried out under slightly aerobic condition at 37° C. for 48 hours with shaking, and then growth of Helicobacter pylori was examined. Antibacterial activity was recorded as the lowest concentration that exhibited growth inhibition (minimum inhibitory concentration: MIC). The results are shown in Tables 3 and 4. From the results shown in Tables 3 and 4, it can be understood that the compounds of the present invention have potent inhibitory activity against Helicobacter pylori.

TABLE 3

| Example No. (Compound No. in Table 1) | MIC ($\mu$g/ml) |
|---|---|
| 1 (No. 17) | 0.39 |
| 3 (No. 7) | 1.56 |
| 8 (No. 18) | 0.78 |
| 10 (No. 22) | 0.39 |
| 16 (No. 33) | 0.78 |
| 17 (No. 42) | 0.39 |
| 18 (No. 43) | 0.39 |
| 19 (No. 59) | 0.78 |
| 20 (No. 60) | 0.78 |
| 22 (No. 62) | 1.56 |
| 23 (No. 63) | 0.78 |
| 24 (No. 68) | 0.78 |
| 30 (No. 113) | 0.10 |
| 31 (No. 114) | 0.05 |
| 32 (No. 140) | 0.78 |
| 33 (No. 146) | 0.10 |
| 34 (No. 148) | 0.20 |
| 36 (No. 159) | 0.78 |
| 38 (No. 177) | 0.78 |
| 41 (No. 191) | 0.10 |
| 42 (No. 192) | 0.39 |
| 43 (No. 204) | 0.39 |
| 44 (No. 216) | 0.78 |
| 45 (No. 219) | 0.78 |
| 49 (No. 246) | 0.78 |

TABLE 4

| Example No. (Compound No. in Table 2) | MIC ($\mu$g/ml) |
|---|---|
| 51 (No. 51) | 0.10 |
| 52 (No. 17) | 0.78 |
| 53 (No. 21) | 0.78 |
| 54 (No. 23) | 0.39 |
| 55 (No. 27) | 0.20 |
| 56 (No. 29) | 0.20 |
| 57 (No. 35) | 0.20 |
| 58 (No. 41) | 0.39 |
| 59 (No. 47) | 0.39 |
| 60 (No. 49) | 0.39 |
| 61 (No. 57) | 0.78 |
| 62 (No. 61) | 0.78 |
| 63 (No. 65) | 0.78 |
| 65 (No. 81) | 0.05 |
| 66 (No. 89) | 0.10 |
| 70 (No. 5) | 1.56 |

Test Example 2

Measurement of Anti-Campylobacter Jejuni Activity

According to a aimiar method to that of Test Example 1, inhibitory activity of the compound of the present invention against Campylobacter jejune was determined. As a result, MIC of the compound of Example 31 was 0.008 $\mu$g/ml. From the result, it can be understood that the compound of the present invention has potent inhibitory activity against Campylobacter jejumni.

Test Example 3

Acute Toxicity Test

The compound of the present invention, suspended in 0.5% CMC-Na aqueous solution, was forcibly administered orally to SD male and female rats, and symptoms of the rats were observed for seven days. As a result, each of $LD_{50}$ values of the compounds of Examples 30 and 31 was not lower than 2,000 mg/kg.

Formulation Examples (1) Tablet

The following ingredients were mixed according to a conventional method, and compressed to obtain a tablet by using a conventional apparatus.

| Compound of Example 31 | 100 mg |
|---|---|
| Crystalline cellulose | 180 mg |
| Corn Starch | 300 mg |
| Lactose | 600 mg |
| Magnesium stearate | 15 mg |

(2) Soft capsule

The following ingredients were mixed according to a conventional method, and filled in a soft capsule.

| Compound of Example 41 | 100 mg |
|---|---|
| Olive oil | 900 mg |
| Lecithin | 60 mg |

Industrial Applicability

The amide derivatives of the present invention have potent antibacterial activity against Helicobacter pylori, and therefore, they are useful as an active ingredient of medicaments.

What is claimed is:

1. A compound represented by the following general formula (I):

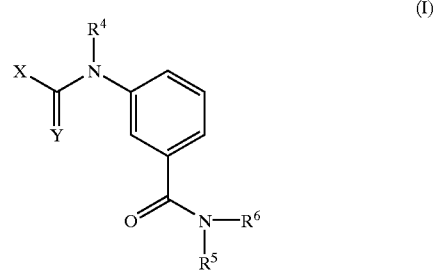

(I)

wherein X represents $R^1(R^2)(R^3)C$— where $R^1$ represents a $C_3$–$C_8$ cycloalkyl group, an optionally substituted $C_6$–$C_{14}$ aryl group, an optionally substituted $C_6$–$C_{14}$ aryloxy group, or an optionally substituted $C_7$–$C_{15}$ arylmethyl group; $R^2$ and $R^3$ independently represent hydrogen atom or a $C_1$–$C_5$ alkyl group, or $R^2$ and $R^3$ may combine to represent a $C_2$–$C_7$ alkylene group; or X represents $R^7$—A— wherein $R^7$ represents (i) a C1–C10 alkyl group which may optionally be substituted with an optionally substituted C6–C14 aryl group, or an optionally substituted fluorenyl group, or (ii) an optionally substituted C6–C14 aryl group, and A represents an oxygen atom or —N—$R^8$ where $R^8$ represents hydrogen atom or a C1–C5 alkyl group, Y represents an oxygen atom or a sulfur atom, $R^4$ represents hydrogen atom or a $C_1$–$C_5$ alkyl group; $R^5$ represents hydrogen atom; and $R^6$ represents a $C_1$–$C_2$ alkyl group which may optionally be substituted with a hydroxyl group, a hydroxyl group or a $C_1$–$C_2$ alkoxy group, provided that the compounds wherein $R^7$ is a benzyl group, A and Y are an oxygen atom, $R^4$ and $R^5$ are hydrogen atom, and $R^6$ is a propyl group are excluded, or a salt thereof or a solvate thereof or a hydrate thereof.

2. The compound according to claim 1 or a salt thereof, or a solvate thereof or a hydrate thereof, wherein $R^4$ is hydrogen atom.

3. The compound according to claim 1 or a salt thereof, or a solvate thereof or a hydrate thereof, wherein $R^6$ is a $C_1$–$C_2$ alkyl group.

4. The compound according to claim 3 or a salt thereof, or a solvate thereof or a hydrate thereof, wherein $R^6$ is methyl group.

5. The compound according to claim 1 or a salt thereof, or a solvate thereof or a hydrate thereof, wherein Y is an oxygen atom.

6. The compound according to claim 5 or a salt thereof, or a solvate thereof or a hydrate thereof, wherein X is $R^1(R^2)(R^3)C$—.

7. The compound according to claim 6 or a salt thereof, or a solvate thereof or a hydrate thereof, wherein $R^2$ and $R^3$ are hydrogen atoms.

8. The compound according to claim 6 or a salt thereof, or a solvate thereof or a hydrate thereof, wherein $R^1$ is a $C_6$–$C_{14}$ aryl group which may optionally be substituted.

9. The compound according to claim 6 or a salt thereof, or a solvate thereof or a hydrate thereof, wherein $R^1$ is a $C_6$–$C_{14}$ aryloxy group which may optionally be substituted.

10. The compound according to claim 6 or a salt thereof, or a solvate thereof or a hydrate thereof, wherein $R^1$ is a $C_7$–$C_{16}$ arylmethyl group which may optionally be substituted.

11. The compound according to claim 1 or a salt thereof, or a rolvate thereof or a hydrate thereof, wherein X is $R^7$—A—.

12. The compound according to claim 11 or a salt thereof, or a solvate thereof or a hydrate thereof, wherein A is an oxygen atom or —N—H.

13. The compound according to claim 11 or a salt thereof, or a solvate thereof or a hydrate thereof, wherein $R^7$ is a C1 to C10 alkyl group which may optionally be substituted with an opionally substituted C6–C14 aryl group.

14. The compound according to claim 13 or a salt thereof, or a solvate thereof or a hydrate thereof wherein $R^7$ is a C1 to C5 alkyl group which may optionally be substituted with an optionally substituted C6–C14 aryl group.

15. The compound according to claim 14 or a salt thereof, or a solvate thereof or a hydrate thereof, wherein $R^7$ is a methyl group which may optionally be substituted with an optionally substituted C6–C14 aryl group.

16. The compound according to claim 15 or a salt thereof, or a solvate thereof or a hydrate thereof, wherein $R^7$ is a methyl group which is substituted with an optionally substituted C6–C14 aryl group.

17. A compound selected from the group consirting of:

N'-methyl-3-(2-chlorobenzyloxycarbonylamino) benzamide;

N'-methyl-3-(4-chlorobenzyloxycarbonylamino) benzamide;

N'-methyl-3-(2, 3-dichlorobenzyloxycarbonylamino) benzamide;

N'-methyl-3-(2, 6-dichlorobenzyloxycarbonylamino) benzamide;

N'-methyl-3-(2-bromobenzyloxycarbonylamino) benzamide;

N'-methyl-3-(2-methylbenzyloxycarbonylamino) benzamide;

N'-methyl-3-(3-methylbenzyloxycarbonylamino) benzamide;

N'-methyl-3-(4-methylbenzyloxycarbonylamino) benzamide;

N'-methyl-3-(1-naphthylmethoxycarbonylamino) benzamide; and

N'-methyl-3-(2-naphthylmethoxycarbonylamino) benzamide;

or a pharmaceutically acceptable salt thereof, or a solvate thereof or a hydrate thereof.

18. N-(3-methylcarbamoylphenyl)-1-naphthylacetamide or a pharmaceutically acceptable salt thereof, or a solvate thereof or a hydrate thereof.

19. N-(3-methylcarbamoylphenyl)-2-naphthylacetanide or a pharmaceutically acceptable salt thereof, or a solvate thereof or a hydrate thereof.

20. N-(3-methylcarbamoylphenyl)-1-naphthyloxyacetamide or a pharmaceutically acceptable salt thereof, or a solvate thereof or a hydrate thereof.

21. A medicament comprising as an active ingredient a substance selected from the group consisting of a compound according to claim 1 and a salt thereof, and a solvate thereof and a hydrate thereof.

22. The medicament according to claim 21 which is in the form of a pharmaceutical composition comprising said substance as an active ingredient and one or more pharmaceutical additives.

23. The medicament according to claim 21 which has antibacterial activity.

24. The medicament according to claim 23 which has antibacterial activity against a microorganism belonging to the genus Helicobacter and/or Campylobacter.

25. The medicament according to claim 24 which has anti-Helicobacter pylori activity and/or anti-Campylobacter jejuni activity.

26. A process for at least one of preventing and treating a digestive disease, comprising administering the medicament according claim 21.

27. The process of claim 26 wherein the digestive disease is one of gastritis, gastric ulcer, gastric cancer, gastric malignant lymphoma, MALT lymphoma, duodenal ulcer, duodenal carcinoma, and enteritis.

28. A process for preventing recurrence of a digestive disease, comprising administering the medicament according to claim 21.

29. The process of claim 28 wherein the digestive disease is one of gastric ulcer and duodenal ulcer.

* * * * *

UNITED STATES PATENT AND TRADEMARK OFFICE
CERTIFICATE OF CORRECTION

PATENT NO. : 6,444,849 B1
DATED : September 3, 2002
INVENTOR(S) : R. Ando et al.

It is certified that error appears in the above-identified patent and that said Letters Patent is hereby corrected as shown below:

Column 97,
Line 8, after "salt thereof" insert -- , --.
Line 35, "$C_7$-$C_{16}$" should be -- $C_7$-$C_{15}$ --.
Line 46, "opionally" should be -- optionally --.

Column 98,
Line 26, "naphthylacetanide" should be -- naphthylacetamide --.
Line 51, after "claim 26" insert -- , --.
Line 58, after "claim 28" insert -- , --.

Signed and Sealed this

Tenth Day of June, 2003

JAMES E. ROGAN
*Director of the United States Patent and Trademark Office*